US012760350B2

(12) United States Patent
Franke

(10) Patent No.: US 12,760,350 B2
(45) Date of Patent: Oct. 13, 2026

(54) KITS AND ASSAYS FOR DETERMINING BACTERIAL CELL VIABILITY

(71) Applicant: Josef D Franke, Omaha, NE (US)

(72) Inventor: Josef D Franke, Omaha, NE (US)

(73) Assignee: Josef D. Franke, Omaha, NE (US)

( * ) Notice: Subject to any disclaimer, the term of this patent is extended or adjusted under 35 U.S.C. 154(b) by 260 days.

(21) Appl. No.: 17/513,867

(22) Filed: Oct. 28, 2021

(65) Prior Publication Data

US 2022/0136033 A1 May 5, 2022

Related U.S. Application Data

(60) Provisional application No. 63/108,318, filed on Oct. 31, 2020.

(51) Int. Cl.

| | |
|---|---|
| ***C12Q 1/06*** | (2006.01) |
| ***C12Q 1/14*** | (2006.01) |
| ***G01N 1/30*** | (2006.01) |
| ***G01N 15/01*** | (2024.01) |
| ***G01N 15/10*** | (2024.01) |
| ***G01N 15/1434*** | (2024.01) |

(52) U.S. Cl.

CPC ................. *C12Q 1/06* (2013.01); *C12Q 1/14* (2013.01); *G01N 1/30* (2013.01); *G01N 15/1434* (2013.01); *G01N 2001/302* (2013.01); *G01N 15/01* (2024.01); *G01N 2015/1006* (2013.01)

(58) Field of Classification Search

CPC ... C12Q 1/06; C12Q 1/14; G01N 1/30; G01N 15/1434; G01N 15/01; G01N 2001/302; G01N 2015/1006; G01N 15/1459; G01N 2015/1402; G01N 2015/1486; G01N 2015/1488

See application file for complete search history.

(56) References Cited

PUBLICATIONS

Stomphorst et al. (J Phys Chem A, 2001, 105:4235-4240) (Year: 2001).*

Zogorski et al. (J Env Sci Health A, 1976, 11:501-505, abstract) (Year: 1976).*

Crini (Bioresource Technol, 2006, 97:1061-1085) (Year: 2006).*

Franke et al. (Biotechniques, 2020, 68:7-13) (Year: 2020).*

Liu et al. (Mat Chem Phys, 2020, 255: 123564-123573) (Year: 2020).*

Ma et al. (Analytica Chim Acta, 1996, 333:86) (Year: 1996).*

Olson et al. (Curr Prot Pharmacol, 2007, A.3A.1) (Year: 2007).*

Sharma et al. (Appl Water Sci, 2011, 1:135) (Year: 2011).*

Philips et al. (Tissue Culture, 1973, Chapter 3—Dye Exclusion Tests for Cell Viability, p. 406-408) (Year: 1973).*

Lisa C. Crowley et al., Dead Cert: Measuring Cell Death by Trypan Blue Uptake and Light Microscopy, Cold Spring Harbor Protocols, 2016(7).

Magdalena Kwolek_Mirek et al., Comparison of Methods Used for Assessing the Viability and Vitality of Yeast Cells, FEMS Yeast Research.

Lina Boulos et al., Live/Dead BacLight: application of a new rapid staining method for direct enumeration of viable and total bacteria in d.

Michael Berney et al., Assessment and Interpretation of Bacterial Viability by Using the Live/Dead BacLight Kit in combination with flow.

Marko Virta et al., Determination of Complement-mediated Killing of Bacteria by Viability Staining and Bioluminescence, Applied and.

Philipp Stiefel et al., Critical Aspects of Using Bacterial Cell Viability Assays with the fluorophores SYTO9 and Propidium Iodide, BMC.

S.M. Stocks, Mechanism and Use of the Commercially Available Viability Stain, BacLight, Cytometry A, 2004, 61(2), 189-195.

Merilin Rosenberg et al., Propidium Iodide Staining Underestimates Viability of Adherent Bacterial Cells, Scientific Reports, 2019, 9(1).

Lutz Netuschil et al., Confusion Over Live/Dead Stainings for the Detection of Vital Microorganisms in Oral Biofilms—which stain is suitable?

Sandra Wiegand et al., On the Maverick Planctomycetes, FEMS Microbiology Review, 2018, 32(10), 739-760.

James Oliver, Recent Findings on the Viable but Nonculturable State in Pathogenic Bacteria, FEMS Microbiology Review, 2010, 34(4), 415-425.

Soo in Kim et al., Application of a Nonhazardous Vital Dye for Cell Counting with Automated Cell Counters, 2016, 492, 8-12.

* cited by examiner

*Primary Examiner* — David Steadman
*Assistant Examiner* — Joseph R Spangler

(57) ABSTRACT

Provided herein are kits comprising (a) erythrosin B (EB); (b) adsorbent; and (c) instructions for use. Also provided are methods of determining the percentage of dead bacteria in a bacterial cell population. The methods comprise (a) obtaining a bacterial cell population; (b) contacting the bacterial cell population with an erythrosin B (EB) solution; (c) contacting the bacterial cell population and EB with an adsorbent to remove excess EB; (d) transferring the non-adsorbed bacterial cell population and EB solution; and (e) determining the percentage of dead bacteria in the bacterial cell population.

23 Claims, 19 Drawing Sheets
(12 of 19 Drawing Sheet(s) Filed in Color)

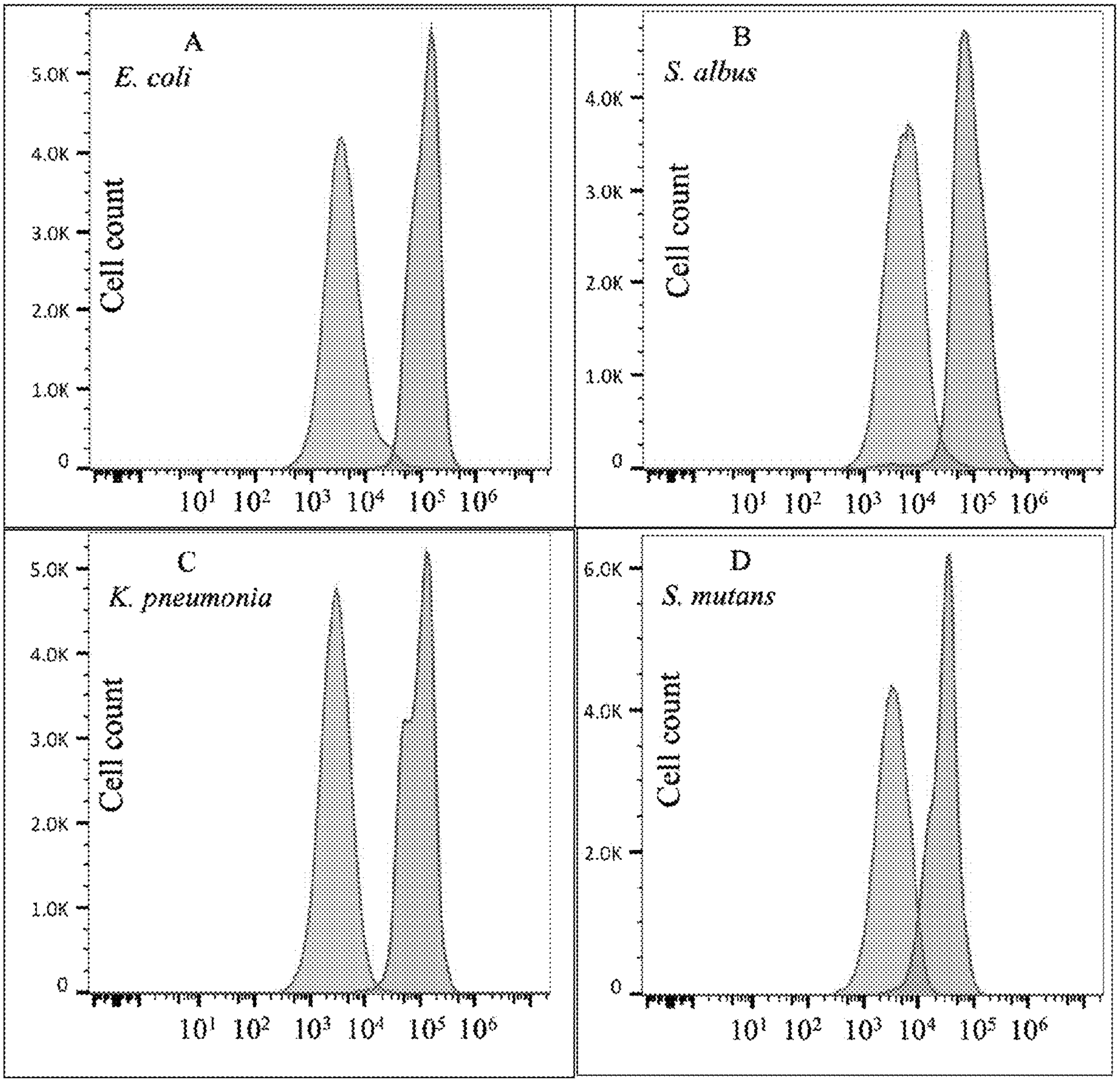
FIGs. 4A-D

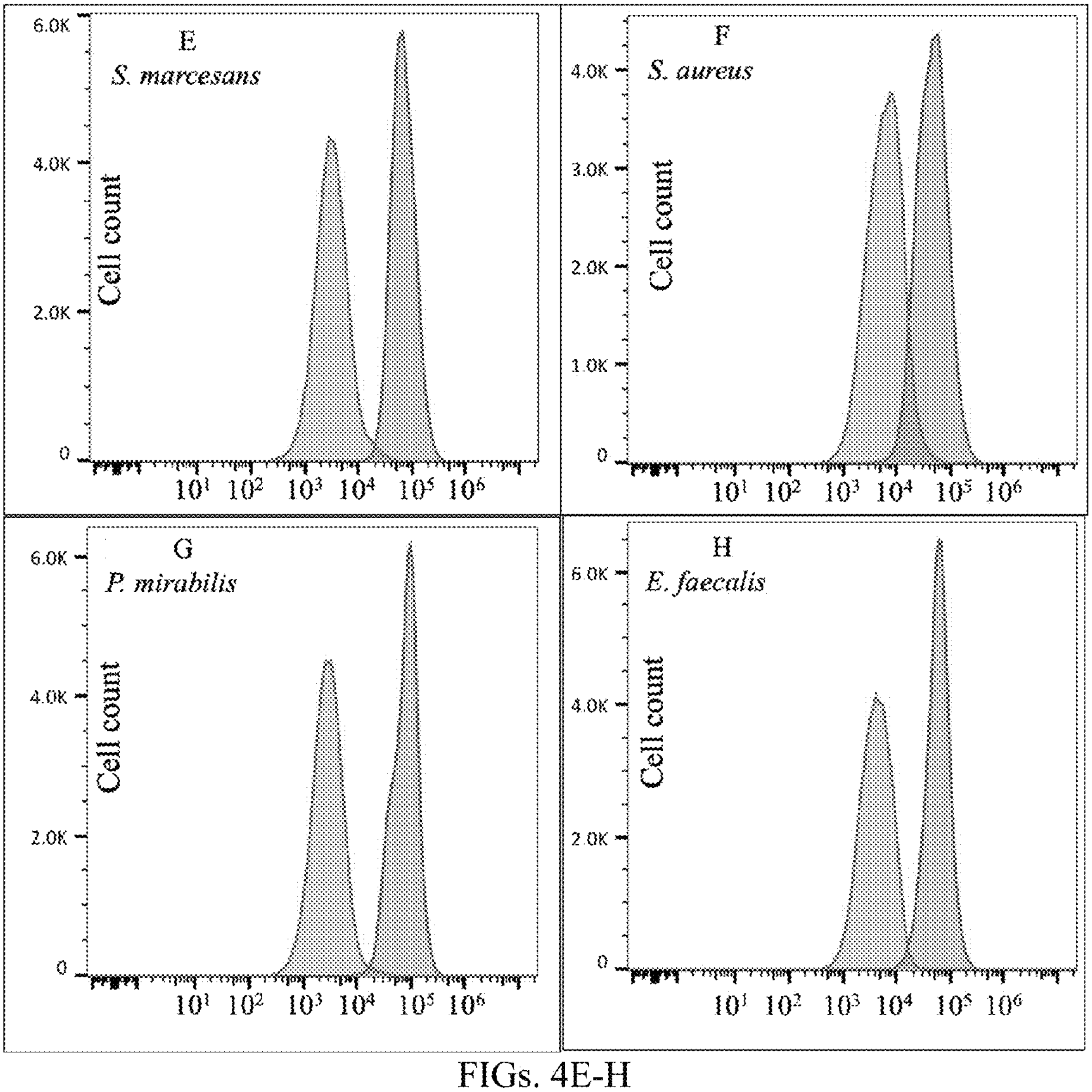
FIGs. 4E-H

| | Percent of cells that are dye-negative | St. dev |
|---|---|---|
| New dye / New resin | 42.0 | 0.32 |
| Old dye / New resin | 42.5 | 0.46 |
| New dye / Old resin | 43.0 | 0.82 |

This image was generated using a publically available website for comparing the fluorescent spectra of dyes and proteins – fpbase.org.

KITS AND ASSAYS FOR DETERMINING BACTERIAL CELL VIABILITY

CROSS REFERENCE TO RELATED APPLICATION

This application claims priority to U.S. Provisional Application No. 63/108,318, filed on Oct. 31, 2020, the disclosure of which is incorporated herein by reference in its entirety.

FIELD OF THE INVENTION

The present invention is directed generally to the field of microbiology. More particularly, the present invention is directed to the kits comprising erythrosin B (EB) for use in methods of determining bacterial cell viability.

BACKGROUND

Determining cell viability is fundamental to many cellular biological studies. Due to their ease of use, low cost, and rapid results, numerous dyes are commonly used for cell viability determination in eukaryotic cells. Membrane exclusion dyes (e.g., trypan blue and propidium iodide) are rapid and enter cells with compromised plasma membranes, such that dye positive cells are scored as dead (1,2). Other dyes, such as fluorescein diacetate (FDA) or methylene blue, indicate the viability of a cell based on a particular metabolic activity (3,4). For these dyes, the initially incubated dye is chemically altered by cellular enzymes. This results in a modified dye, with new spectral properties, that indicates living cells with metabolic activity. This diversity of eukaryotic dyes allows for cell viability to be determined based on the characteristics of either living cells or dead cells and using either colorimetric or fluorescence-based methods of detection.

Unlike eukaryotic cells, rapid colorimetric vital dyes are not routinely used to assay cell viability in bacteria. Propidium iodide can be used as a vital dye in combination with other dyes that stain all cells (e.g., SYTO9™) forming the basis of different live/dead assays such as the widely used BacLight™ kit (5). There are disadvantages to the BacLight™ kits in that the kits are costly and require expensive fluorescence quantitation equipment. Also, in these assays, cells do not always fall into discrete live or dead categories as intermediate populations are possible (6,7). Additionally, depending on the bacterial species being investigated, the concentration of each dye, and the relative ratio of the two dyes, often requires optimization (8,9). As a result, these kits are not well suited for field work, research involving multiple species, or adherent cells in biofilms (10,11).

Alternatively, bacterial cell viability can be determined by the presence of colony forming units (CFU method, (4)). Here, dilute solutions of cells are spread on agar plates and the number of colonies are counted after an incubation period and compared to control plates. This method has two significant drawbacks. First, the proportion of dead cells in a population can be overestimated because the method requires that all viable cells undergo sufficient rounds of division to form a visible colony. Living cells unable to divide, or dividing slower than controls, will be incorrectly scored as dead if they fail to divide sufficiently and form a colony in the appropriate amount of time. Second, the CFU method is particularly time consuming when working with slow growing bacteria in which colony formation takes several days, resulting in undesirable waiting periods between experiments.

To date, there are no colorimetric bacterial vital dyes available to researchers. The lack of bacterial vital dyes available for researchers is a long felt, but unmet need in the field of bacterial viability. Identifying bacterial vital dyes would save time and allow bacterial viability to be determined by light microscopy. The bacterial vital dyes could be used in experiments ranging from routine viability assays to high-throughput screens identifying novel bactericidal compounds and analyzing multi-species samples.

SUMMARY

As demonstrated herein, erythrosin B, a dye with colorimetric and fluorescent properties, functions as an indicator of bacterial viability. Erythrosin B staining is rapid and functions at a single concentration for diverse species of bacteria. The dye is inexpensive and allows for live/dead determination in both colorimetric and fluorescence-based assays for low, medium, and high-throughput experimentation.

In one general aspect, provided herein is a kit comprising (a) erythrosin B (EB); (b) adsorbent; and (c) instructions for use.

In certain embodiments, the kit further comprises a buffer. The buffer can, for example, be selected from a Tris buffer or a phosphate buffer.

In certain embodiments, the EB is in solution. The concentration of EB solution can, for example, be about 0.01% to about 0.5%. The concentration of EB solution can, for example, be about 0.05% to about 0.2%. In certain embodiments, the concentration of EB solution is about 0.08%.

In certain embodiments, the adsorbent comprises a hydrophobic moiety. The hydrophobic moiety can, for example, be selected from a divinylbenzene moiety or a polydivinylbenzene moiety. In certain embodiments, the adsorbent is linked to a bead, a membrane, a plate, or a resin. Preferably the adsorbent is linked to a bead.

Also provided are methods of determining the percentage of dead bacteria in a bacterial cell population. The methods comprise (a) obtaining a bacterial cell population; (b) contacting the bacterial cell population with an erythrosin B (EB) solution; (c) contacting the bacterial cell population and EB with an adsorbent to remove excess EB; (d) transferring the non-adsorbed bacterial cell population and EB solution; and (e) determining the percentage of dead bacteria in the bacterial cell population.

In certain embodiments, the concentration of EB solution is about 0.01% to about 0.5%. The concentration of EB solution can, for example, be about 0.05% to about 0.2%. In certain embodiments, the concentration of EB solution is about 0.08%. The concentration of EB solution can, for example, be about 0.01%, about 0.02%, about 0.03%, about 0.04%, about 0.05%, about 0.06%, about 0.07%, about 0.08%, about 0.09%, about 0.1%, about 0.11%, about 0.12%, about 0.13%, about 0.14%, about 0.15%, about 0.16%, about 0.17%, about 0.18%, about 0.19%, or about 0.2%, or any value in between.

In certain embodiments, the adsorbent comprises a hydrophobic moiety. The hydrophobic moiety can, for example, be selected from a divinylbenzene moiety or a polydivinylbenzene moiety. In certain embodiments, the adsorbent is linked to a bead, a membrane, a plate, or a resin. Preferably, the adsorbent is linked to a bead.

In certain embodiments, the adsorbent is at a concentration of about 0.08 mg/mL to about 2.0 mg/mL. The adsorbent can, for example, be about 0.08 mg/mL, about 0.1 mg/mL, about 0.2 mg/ml, about 0.3 mg/mL, about 0.4 mg/mL, about 0.5 mg/mL, about 0.6 mg/mL, about 0.7 mg/mL, about 0.8 mg/mL, about 0.9 mg/mL, about 1.0 mg/mL, about 1.1 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, about 1.9 mg/mL, or about 2.0 mg/mL or any value in between.

In certain embodiments, the method further comprises a step of contacting the transferred non-adsorbed bacterial cell population and EB solution with an event marker. The event marker can, for example, be selected from a DNA binding marker, a metabolic marker, a cell surface marker, or a general fluorescent marker.

In certain embodiments, a plate reader, a flow cytometer, an automated cell counter, or a microscope is used to determine the percentage of dead bacteria in the bacterial cell population. A colony forming unit (CFU) assay can also be performed and a microscope can, for example, be a light microscope or a fluorescence microscope.

BRIEF DESCRIPTION OF FIGURES

The patent or application file contains at least one drawing executed in color. Copies of this patent or patent application publication with color drawing(s) will be provided by the Office upon request and payment of the necessary fee.

The foregoing summary, as well as the following detailed description of the invention, will be better understood when read in conjunction with the appended drawings. It should be understood that the invention is not limited to the precise embodiments shown in the drawings.

(FIG. 3A) Equal amounts of all *P. mirabilis* cell mixtures and controls (cells not exposed to EB, −EB) were transferred into separate wells of a 96-well plate and imaged to show the colorimetric variation of these different mixtures. (FIG. 3B-3D) Comparable experiments were done with *E. coli* and *K. pneumoniae* and $A_{530}$ values were collected for all three organisms and their mixtures. Control values (from boxed wells) were subtracted from each experimental value. The means and standard deviations were calculated for each mixture condition and plotted. Linear trends were observed for all species with $R^2$ values as follows: *E. coli* (0.992), *P. mirabilis* (0.987) and *K. pneumoniae* (0.997).

FIGS. 4A-4H: Distinguishing between live cell populations and dead cell populations via EB fluorescence. Clear differences in EB fluorescence intensity were observed when live cells (green plots) and dead cells (red plots) were analyzed by flow cytometry. In these assays, dead cells were prepared by ethanol exposure. Both Gram-negative bacteria (left panels) and Gram-positive bacteria (right panels) exhibited these differences. All flow cytometry plots indicate the number of cells analyzed on the Y-axis and the fluorescence intensity (em. 583/30; $\log_{10}$ scale) on the X-axis. A minimum of 100,000 cells were analyzed for each species under each condition.

FIG. 7A: Tubes were prepared containing solutions of either bacterial cells or buffer as labelled. FIG. 7B: EB dye solution was added to all tubes except the "Cells" tube (buffer was added to this tube) and incubated at room temperature. FIG. 7C: Adsorbent resin was added to all tubes followed by constant agitation at room temperature. After agitation, tubes were left to allow resin to settle by gravity. FIG. 7D: The non-adsorbed solutions were transferred to new tubes. Note the lack of color in the buffer tube demonstrating the adsorbent bound excess EB dye in solution and that the amount of color in this tube is comparable to the "Live cells" tube. Additionally, the increased red color observed in the "Dead cells" tube compared to the "Live cells" tube shows that the dead cells retained more dye that live cells.

FIG. 8A: Different Live/Dead ratios of *E. coli* cells were prepared (0%, 25%, 50%, 75%, and 100% Dead). The cells were stained with EB and then mixtures were incubated with an adsorbent. The non-adsorbed material was then assayed via a plate reader to quantify the absorbance at 530 nm ($A_{530}$). Similar to EB-only staining of this organism (FIG. 3B), an increasing, linear relationship of dead cells to dye was observed. FIG. 8B: Live *E. coli* cells were incubated with EB dye and the mixture was adsorbed with resin. The unadsorbed material was visualized and imaged on a light microscope. The live cells did not retain sufficient EB dye to alter their visual appearance. FIG. 8C: Dead *E. coli* cells were incubated with EB dye and the mixture was adsorbed with resin. The unadsorbed material was visualized and imaged on a light microscope. The dead cells did retain sufficient EB dye to alter their appearance becoming reddish in color (similar to EB-only staining FIG. 1). FIG. 8D. *E. coli* cells from the 0% Dead sample were viewed and imaged with a light microscope. These cells were dye-negative as expected for a sample with only living cells. FIG. 8E. *E. coli* cells from the 100% Dead sample were viewed and imaged with a light microscope. These cells were all dye-positive which is expected for dead cells.

FIG. 12A: A predominantly live cell population was stained with EB, incubated with an adsorbent, and then the unadsorbed materials were analyzed by flow cytometry. EB-negative cells (lower left quadrant) are living cells, while EB-positive cells (upper left quadrant) are dead cells. FIG. 12B: A live population of cells was incubated with SYTO9™, a common membrane-permeable DNA-stain used to identify both live and dead bacteria. SYTO9™-dye positive cells are present in the lower-right quadrant. FIG. 12C: A predominantly live population of cells was first stained with EB (similar to FIG. 12A) and then incubated with SYTO9™. Most cells were SYTO9™ dye-positive and EB dye-negative and present in the lower-right quadrant. FIG. 12D: A dead cell population was first stained with EB (similar to FIG. 12A) and then incubated with SYTO9™. The dead cell population is shifted on both axes to the upper-right quadrant as these cells are both EB-positive and SYTO9™-positive.

DETAILED DESCRIPTION

Figure 1:
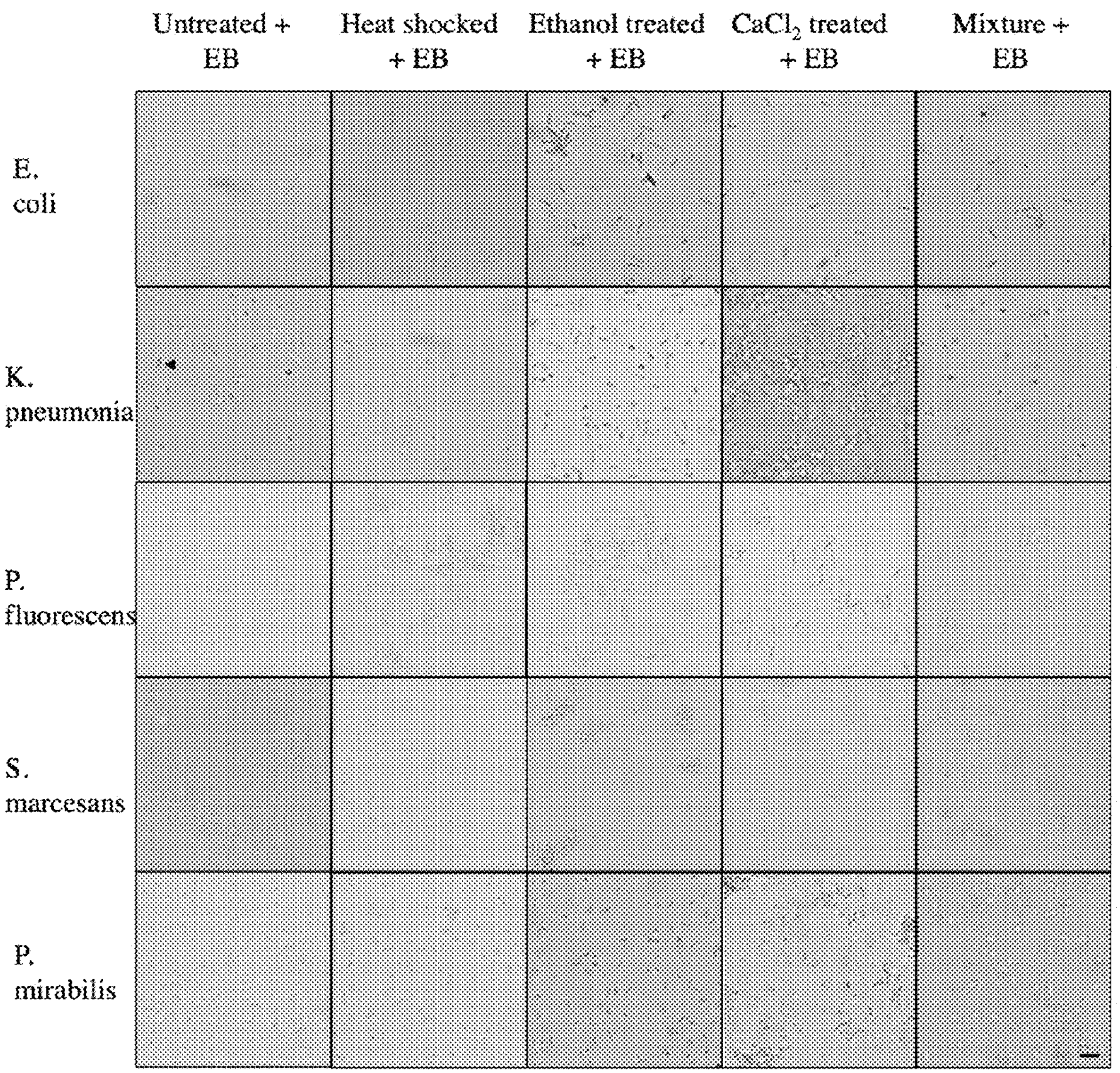
FIG. 1: Erythrosin B functions as a vital dye specifically staining dead, or membrane-compromised, Gram-negative bacteria. Bacterial cells were incubated with erythrosin B (+EB) prior to, or after, heat-shock, ethanol treatment, or $CaCl_2$ incubation. Images in the "Mixture" column were taken of cell suspensions containing equal amounts of live, untreated cells and dead cells (either heat-shocked or ethanol-treated). Mixtures were incubated with EB and images show the ability to distinguish between living (dye-negative) and dead (dye-positive) cells. An arrowhead in the (*K. pneumoniae*) untreated control image indicates a clearly distinguishable dye-positive, dead cell among dye-negative cells further demonstrating the visible difference in staining between dye-positive and dye-negative cells. The scale bar in the bottom right panel is 5 μm and applies to all panels.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains," or "containing," or any variation thereof, will be understood to imply the inclusion of a stated integer or integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure, or composition. See M.P.E.P. § 2111.03.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systemic errors, manufacturing tolerances, etc.), would not vary the least significant digit.

Kits and Methods for Assaying Bacterial Cell Viability

The present invention relates generally to the identification and use of erythrosin B (EB) for assaying bacterial cell viability. Rapidly assaying cell viability for diverse bacteria species is not always straightforward. In eukaryotes, cell viability is often determined using colorimetric dyes; however, such dyes have not been identified for bacteria. As demonstrated herein, erythrosin B (EB), a visibly red dye with fluorescent properties, functions as a vital dye for Gram-positive and Gram-negative bacteria. Erythrosin B worked at a similar concentration for all bacteria studied and incubations were as short as five minutes. Given erythrosin B's spectral properties, diverse experimental approaches are possible to rapidly visualize and/or quantitate dead bacterial cells in a population. As the first broadly applicable colorimetric viability dye for bacteria, erythrosin B provides a cost-effective alternative for researchers in academia and industry.

In one general aspect, provided herein is a kit comprising (a) erythrosin B (EB); (b) adsorbent; and (c) instructions for use. In certain embodiments, the EB is in a solid form, for example, as a powder, or is in solution in a buffer.

In certain embodiments, if the EB is provided in a solid form, the kit further comprises a buffer. The buffer can, for example, be selected from a Tris buffer or a phosphate buffer.

In certain embodiments, the EB is in solution. The concentration of EB solution can, for example, be about 0.01% to about 0.5%. The concentration of EB solution can, for example, be about 0.05% to about 0.2%. In certain embodiments, the concentration of EB solution is about 0.08%.

In certain embodiments, the adsorbent comprises a hydrophobic moiety. The hydrophobic moiety can, for example, be selected from a divinylbenzene moiety or a polydivinylbenzene moiety. In certain embodiments, the adsorbent is linked to a bead, a membrane, a plate, or a resin. Preferably the adsorbent is linked to a bead.

Also provided are methods of determining the percentage of dead bacteria in a bacterial cell population. The methods comprise (a) obtaining a bacterial cell population; (b) contacting the bacterial cell population with an erythrosin B (EB) solution; (c) contacting the bacterial cell population and EB with an adsorbent to remove excess EB; (d) transferring the non-adsorbed bacterial cell population and EB solution; and (e) determine the percentage of dead bacteria in the bacterial cell population.

In certain embodiments, the concentration of EB solution is about 0.01% to about 0.5%. The concentration of EB solution can, for example, be about 0.05% to about 0.2%. In certain embodiments, the concentration of EB solution is about 0.08%. The concentration of EB solution can, for example, be about 0.01%, about 0.02%, about 0.03%, about 0.04%, about 0.05%, about 0.06%, about 0.07%, about 0.08%, about 0.09%, about 0.1%, about 0.11%, about 0.12%, about 0.13%, about 0.14%, about 0.15%, about 0.16%, about 0.17%, about 0.18%, about 0.19%, or about 0.2%, or any value in between.

In certain embodiments, the adsorbent comprises a hydrophobic moiety. The hydrophobic moiety can, for example, be selected from a divinylbenzene moiety or a polydivinylbenzene moiety. In certain embodiments, the adsorbent is linked to a bead, a membrane, a plate, or a resin. Preferably, the adsorbent is linked to a bead.

In certain embodiments, the adsorbent is at a concentration of about 0.08 mg/mL to about 2.0 mg/mL. The adsorbent can, for example, be about 0.08 mg/mL, about 0.1 mg/mL, about 0.2 mg/ml, about 0.3 mg/mL, about 0.4 mg/mL, about 0.5 mg/mL, about 0.6 mg/mL, about 0.7 mg/mL, about 0.8 mg/mL, about 0.9 mg/mL, about 1.0 mg/mL, about 1.1 mg/mL, about 1.2 mg/mL, about 1.3 mg/mL, about 1.4 mg/mL, about 1.5 mg/mL, about 1.6 mg/mL, about 1.7 mg/mL, about 1.8 mg/mL, about 1.9 mg/mL, or about 2.0 mg/mL or any value in between.

In certain embodiments, the method further comprises a step of contacting the transferred non-adsorbed bacterial cell population and EB solution with an event marker. The event marker can, for example, be a DNA binding marker, a metabolic marker, a cell surface marker, or a general fluorescent marker. Examples of DNA binding markers include, but are not limited to SYTO9™ and thiazole orange. Examples of metabolic markers include, but are not limited to fluorescein diacetate (FDA), carboxyfluorescein diacetate (CFDA), and ChemChrome B. Examples of cell surface markers include, but are not limited to antibodies with fluorescent moieties that are capable of binding a component of the cell surface (e.g., a cell surface protein or carbohydrates). Examples of general fluorescent markers include, but are not limited to, green fluorescent protein, red fluorescent protein, or cyan fluorescent protein.

In certain embodiments, a plate reader, a flow cytometer, an automated cell counter, or a microscope is used to determine the percentage of dead bacteria in the bacterial cell population. A colony forming unit (CFU) assay can also be performed and a microscope can, for example, be a light microscope or a fluorescent microscope.

EMBODIMENTS

Embodiment 1 is a kit comprising:
- a. erythrosin B (EB);
- b. adsorbent; and
- c. instructions for use.

Embodiment 2 is the kit of embodiment 1, wherein the kit further comprises a buffer.

Embodiment 3 is the kit of embodiment 2, wherein the buffer is selected from a Tris buffer or a phosphate buffer.

Embodiment 4 is the kit of embodiment 1, wherein the EB is in solution.

Embodiment 5 is the kit of embodiment 4, wherein the concentration of EB solution is about 0.01% to about 0.5%.

Embodiment 6 is the kit of embodiment 4 or 5, wherein the concentration of EB solution is about 0.05% to about 0.2%.

Embodiment 7 is the kit of embodiment 6, wherein the concentration of EB solution is about 0.08%.

Embodiment 8 is the kit of any one of embodiments 1 to 7, wherein the adsorbent comprises a hydrophobic moiety.

Embodiment 9 is the kit of embodiment 8, wherein the hydrophobic moiety is selected from a divinylbenzene moiety or a polydivinylbenzene moiety.

Embodiment 10 is the kit of embodiment 9, wherein the adsorbent is linked to a bead, a membrane, a plate, or a resin.

Embodiment 11 is the kit of embodiment 10, wherein the adsorbent is linked to a bead.

Embodiment 12 is a method of determining the percentage of dead bacteria in a bacterial cell population, the method comprising:
- a. obtaining a bacterial cell population;
- b. contacting the bacterial cell population with an erythrosin B (EB) solution;
- c. contacting the bacterial cell population and EB with an adsorbent to remove excess EB;
- d. transferring the non-adsorbed bacterial cell population and EB solution; and
- e. determining the percentage of dead bacteria in the bacterial cell population.

Embodiment 13 is the method of embodiment 12, wherein the concentration of EB solution is about 0.01% to about 0.5%.

Embodiment 14 is the method of embodiment 13, wherein the concentration of EB solution is about 0.05% to about 0.2%.

Embodiment 15 is the method of embodiment 14, wherein the concentration of EB solution is about 0.08%.

Embodiment 16 is the method of any one of embodiments 12 to 15, wherein the adsorbent comprises a hydrophobic moiety.

Embodiment 17 is the method of embodiment 16, wherein the hydrophobic moiety is selected from a divinylbenzene moiety or a polydivinylbenzene moiety.

Embodiment 18 is the method of embodiment 17, wherein the adsorbent is linked to a bead, a membrane, a plate, or a resin.

Embodiment 19 is the method of embodiment 18, wherein the adsorbent is linked to a bead.

Embodiment 20 is the method of any one of embodiments 16 to 19, wherein the adsorbent is about 0.08 mg/mL to about 2.0 mg/mL.

Embodiment 21 is the method of any one of embodiments 12 to 20, wherein the method further comprises a step of contacting the transferred non-adsorbed bacterial cell population and EB solution with an event marker.

Embodiment 22 is the method of embodiment 21, wherein the event marker is selected from a DNA binding marker, a metabolic marker, a cell surface marker, or a general fluorescent marker.

Embodiment 23 is the method of any one of embodiments 12 to 22, wherein a plate reader, a flow cytometer, an automated cell counter, a microscope, or a CFU assay is used to determine the percentage of dead bacteria in the bacterial cell population.

Embodiment 24 is the method of embodiment 23, wherein the microscope is a light microscope or a fluorescent microscope.

EXAMPLES

Example 1: Use of Erythrosin B to Determine Bacterial Cell Viability

Methods and Materials

Organisms and reagents. The following bacteria were used in this study: *Bacillus cereus* (Carolina Biological, NC, USA 154870), *Escherichia coli* (MG1655), *Klebsiella pneumoniae* (Carolina Biological, NC, USA 155095A), *Pseudomonas fluorescencs* (Carolina Biological, NC, USA 155255), *Serettia marcesans* (Carolina Biological, NC, USA 155450), *Streptomyces albus* (Ward's Science, NY, USA 470179-180), *Streptococcus mutans* (Ward's Science, NY, USA 470179-582), *Proteus mirabilis* (BB2200), *Staphylococcus aureus* (Carolina Biological, NC, USA 155554), and *Enterococcus faecalis* (Ward's Science, NY, USA 470179-184).

Erythrosin B (EB, Sigma, MO, USA 200964-5G) was prepared by dissolving powder in 10 mM Tris pH 7.5. Published values of the solubility of EB in aqueous solutions vary and may result from different preparations of the dye and from which supplier it is purchased. A small amount of undissolved dye was present when preparing a 0.1% (w/v) solution. This stock solution was filtered through a 0.22 μm filter to remove undissolved dye. To determine the concentration of this stock solution a fresh, dilute EB solution was prepared in which all dye fully dissolved after 10 minutes of stirring. This dilute solution was serially diluted and $A_{530}$ readings (the wavelength of maximal absorbance for EB) were collected generating a reference relating EB dye concentration to $A_{530}$. The filtered, stock solution of EB was then serially diluted, and absorbance values of the dilutions were compared to the reference absorbance values for the dilute solution. The stock EB concentration was determined to be 0.08% and is used throughout this work.

Growth and treatments of bacteria. To prepare cells for viability studies, 3 mL overnight bacterial cultures were grown in Luria Broth. Fresh 5 mL cultures were inoculated from the overnight cultures and grown for 1 to 4 hours until reaching an $OD_{600}$ of 0.4-1.1. Cells were harvested by centrifugation (15,000 g for 4 minutes) and then resuspended in phosphate buffered saline (PBS). A portion of these cells were kept at room temperature (untreated controls), while the remainder were transferred into separate microfuge tubes for different treatments. For heat shock treatment, microfuge tubes were placed at 70° C. for 30 minutes before returning to room temperature. For ethanol treatment, 100% ethanol (Decon Labs, Inc., PA, USA product number 2716) was added to cell suspensions to a final concentration of 30%. Cell mixtures were incubated at 37° C. for 30 minutes, centrifuged, and then the pellet was resuspended in PBS. For $CaCl_2$ treatment, cells were centrifuged, and the pellet was resuspended in 1 mL of ice-cold 100 mM $CaCl_2$ and left on ice for 45 minutes. After this initial incubation, the cells were centrifuged and resuspended in 100 μL of 100 mM $CaCl_2$.

Assaying bacterial viability. For bright-field microscopy assays, 10 μL of each cell suspension (untreated, heat-shocked, ethanol-treated and $CaCl_2$)-treated) was mixed with 10 μL of 0.08% erythrosin B and incubated for 5 minutes at room temperature. For $CaCl_2$)-treated cells, mixtures were placed at 42° C. for 60 seconds before returning to room temperature for the remainder of the incubation. 5 μl of the incubated dye:cell mixtures were taken to prepare wet mounts. Imaging was performed on a Zeiss OLYMPUS™ BX61 microscope using an UPlanSApo 100X/1.14 NA oil objective lens with an OLYMPUS™ SC10 camera.

For plate reading assays, a total of four ODs of log-phase cells were collected and evenly split between two tubes. Cells were centrifuged as described above. One tube was resuspended in 1 mL of PBS (live cells), and the other tube was incubated at 70° C. for 30 minutes (dead cells) before being resuspended in 1 mL of PBS. 100 μl cell mixtures were then prepared in triplicate by mixing appropriate volumes of live and dead cell suspensions to generate the following ratios of live to dead cells: 100% live cells, 75% live cells/25% dead cells, 50% live cells/50% dead cells, 25% live cells/75% dead cells, and 100% dead cells. 100 μl of 0.08% EB was added to all cell mixtures and incubated for 5 minutes. Control cell mixtures, containing 100 μl of live cells or dead cells, were incubated with 100 μl of PBS instead of EB. All mixtures were centrifuged and the supernatant removed. The tubes were briefly spun again and any residual supernatant was removed. Cell pellets were resuspended in 100 μl of PBS, vortexed, and 75 μl of each mixture was transferred to a clear 96-well plate (NUNC™, 80042LE). Absorbance readings (530 nm; $A_{530}$) were taken using a SYNERGY™ H1 hybrid plate reader. Control $A_{530}$ values were subtracted from the experimental $A_{530}$ values prior to calculations.

For flow cytometry assays, different EB-cell suspensions were incubated in the presence of EB for 5 minutes at room temperature, centrifuged, and the cell pellets were resuspended in 1 mL of PBS. To remove excess unbound EB, the cells were washed twice in 1 mL of PBS prior to analysis. For the sodium azide time course, a 5 mL *S. marcesans* culture was grown to an $OD_{600}$ of ~0.2 in Luria Broth at 37° C. Sodium azide was added to a final concentration of 0.07% and 0.5 mL samples were taken at different times points. Each sample was then immediately centrifuged to pellet the bacteria and stained with EB as described above to prepare samples for flow cytometry. A YETI flow cytometer (Propel Labs, Inc., CO, USA) was used to analyze cells (excitation with a 561 nm laser/emission collected using a 583/30 filter).

Results

In eukaryotic cells, erythrosin B (EB) is known to function as a membrane-exclusion vital dye such that dead cells with compromised plasma membranes are dye-positive (12). Despite certain advantages over other traditional colorimetric membrane exclusion dyes (13), the application of EB as a vital dye in eukaryotes is not as wide-spread as other dyes with a comparable mechanism of action (e.g., trypan blue). A practical vital dye for bacteria was sought, and EB was tested due to its intense red color and spectral properties. The intense color would allow for a clear distinction between live and dead cells by bright-field microscopy for small cells like bacteria, and the spectral properties would allow a single dye to be used for cell viability assays measuring either absorbance or fluorescence.

Figure 2:
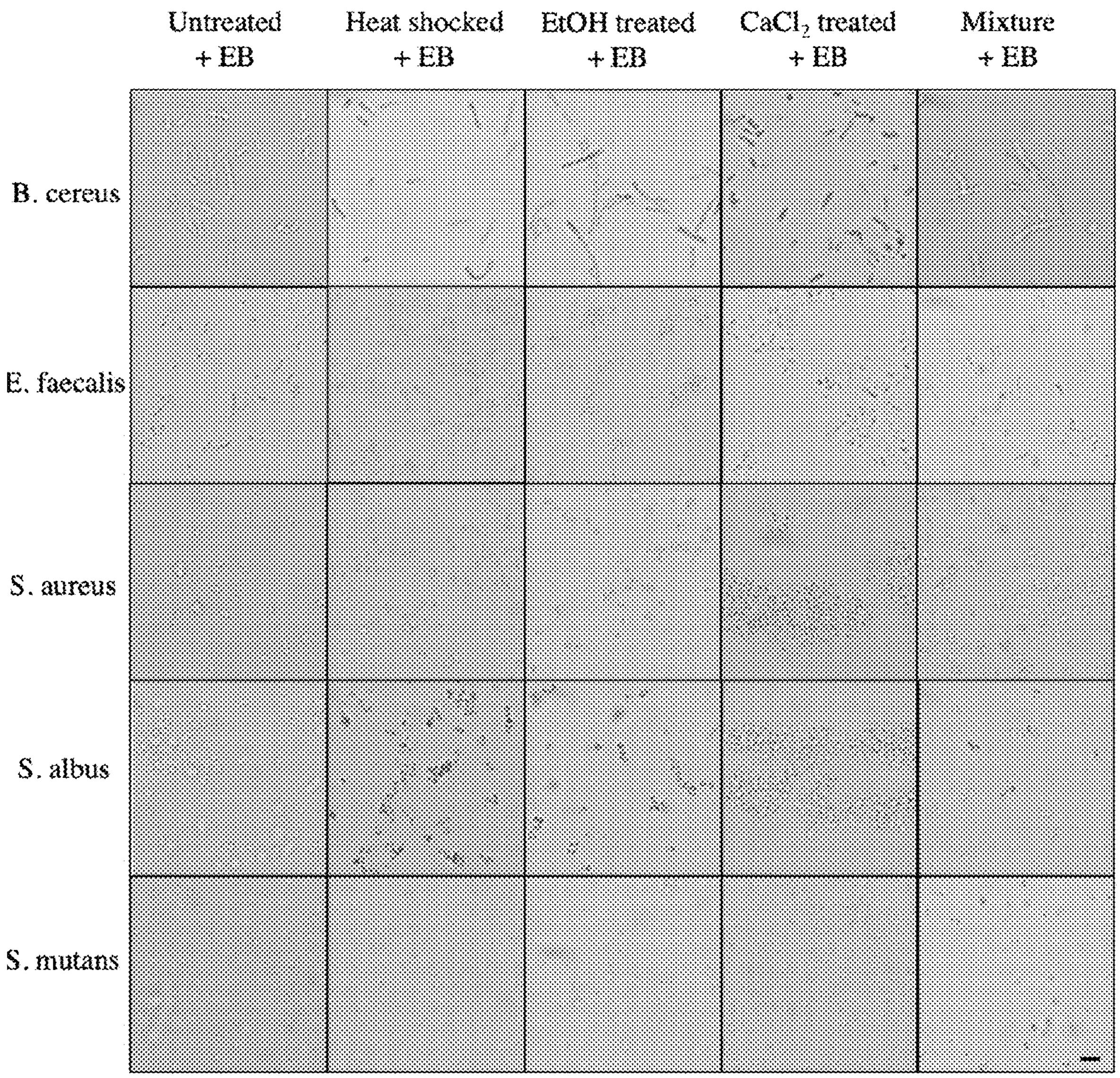
FIG. 2: Erythrosin B functions as a vital dye specifically staining dead, or membrane-compromised, Gram-positive bacteria. Bacterial cells were incubated with EB prior to, or after, heat-shock, ethanol treatment, or $CaCl_2$ incubation. Images in the "Mixture" column were taken of cell suspensions containing equal amounts of live, untreated cells and dead cells (either heat-shocked or ethanol-treated). Mixtures were incubated with EB and images show the ability to distinguish between living (dye-negative) and dead (dye-positive) cells. The scale bar in the bottom right panel is 5 μm and applies to all panels.

A variety of differently-shaped Gram-negative and Gram-positive bacteria were screened. Three different treatments were performed: heat shock, ethanol exposure, and $CaCl_2$ exposure. The treatments were designed to induce cell death (heat shock and ethanol exposure) or affect membrane permeability ($CaCl_2$-exposure) across diverse bacterial species. For all species examined in this study, EB specifically stained dead or membrane compromised Gram-negative (FIG. 1) and Gram-positive bacteria (FIG. 2). For heat shocked and ethanol-treated organisms, virtually all treated cells were dye-positive. For $CaCl_2$-treated cells, not all treated cells were dye positive. $CaCl_2$ treatment was designed to affect membrane permeability, and not cause cell death, and resulted in a variable amount of dye-positive cells for different species. This variability likely reflects inherent species-specific effects of $CaCl_2$ exposure. Increased $CaCl_2$ concentration, incubation time, and/or prolonged heat shock would likely have resulted in a greater proportion of dye-positive cells.

Figure 6:
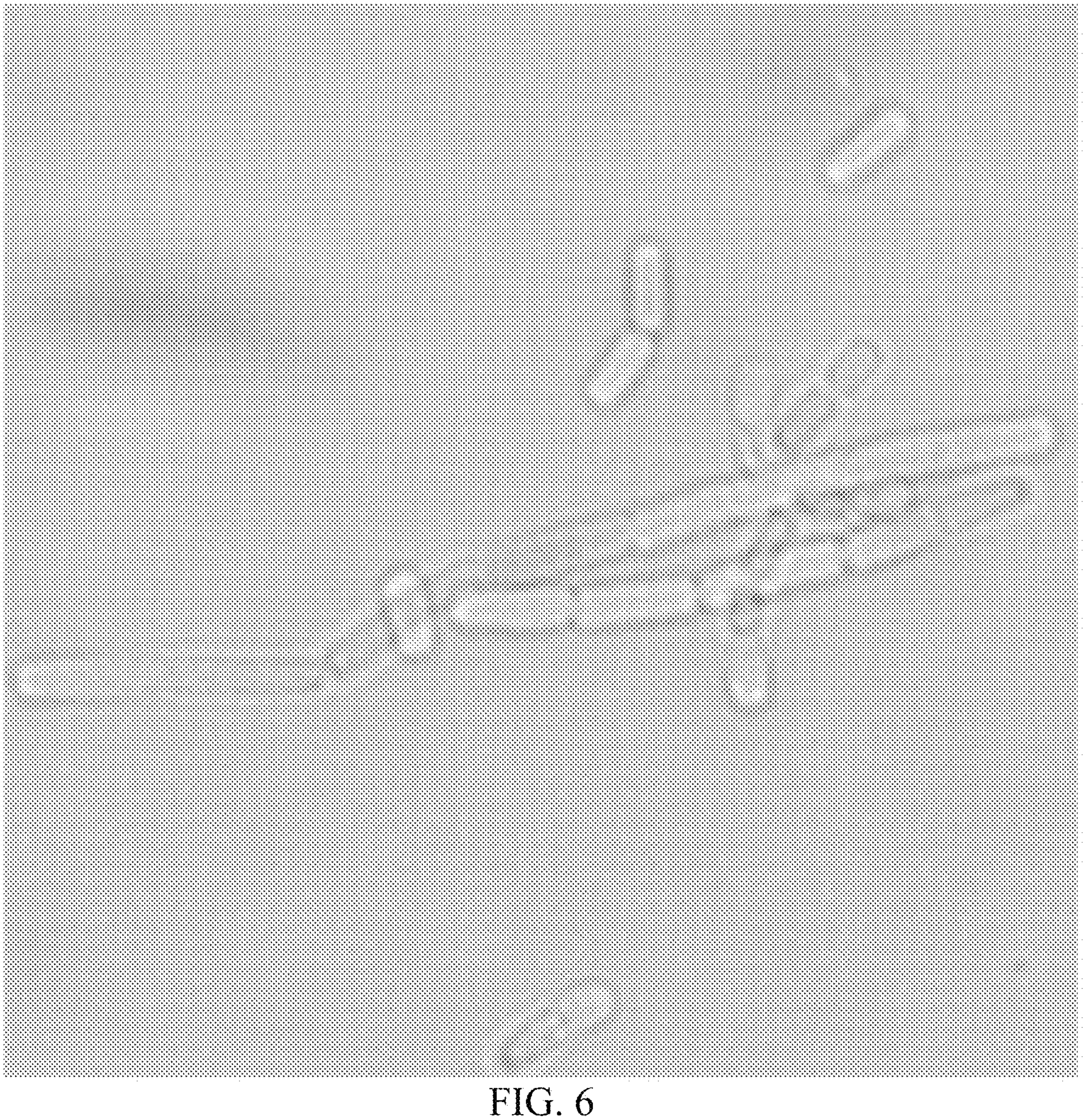
FIG. 6 shows a bright-field image of *B. cereus* cells taken from a stationary phase culture and incubated in a 0.4% EB solution. In two instances EB specifically stains a single compartment (cell) in a filamentous chain.

For all species examined in this study, <3% of healthy cells were dye-positive by bright-field microscopy when incubated with EB (untreated columns in FIG. 1 and FIG. 2) demonstrating EB does not readily stain living bacterial cells. EB-containing cell suspensions were generally viewed after 10 to 15 minutes of dye incubation, though clear differences between dye-negative and dye-positive cells were visible within 5 minutes. Longer incubations, up to 30 minutes, did not affect the ability to distinguish dye-positive from dye-negative cells. Faint staining of live bacteria was sometimes observed in three species (*S. albus, S. mutans*, and *E. faecalis*) after typical incubations. However, the amount of staining in dye-positive, dead cells was clearly increased compared to live cells, making it easy to distinguish between living and dead cells. Importantly, EB can also spatially resolve heterogeneities in the viability of different compartments in filamentous bacteria (FIG. 6), similar to the BacLight™ system (9). Lastly, visualization by bright-field microscopy allows for a rapid and accurate quantitation of dead cells in a sample with a low incidence of dead cells.

Figures 3A, 3B, 3C, 3D:
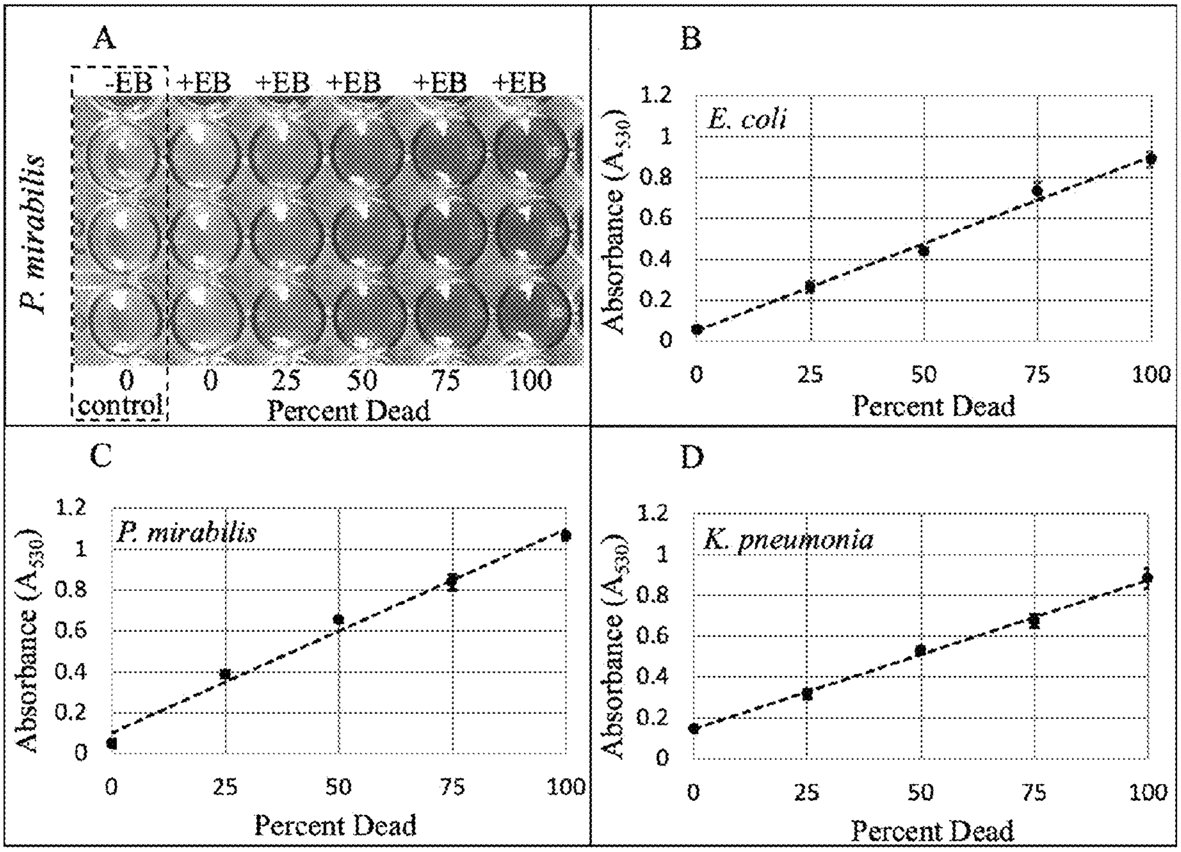
FIGS. 3A-3D: The relative amount of dead cells in a bacterial suspension can be determined using EB absorbance values. Mixtures containing different ratios of cells (0% dead/100% live; 25% dead/75% live; 50% dead/50% live; 75% dead/25% live; and 100% dead/0% live) were prepared and then similarly incubated with EB. In these assays, dead cells were prepared by heat shock. All mixtures were prepared in triplicate, and unbound EB was removed after the incubation.

The ability of EB to function as a general bacterial cell viability indicator was examined in different high-throughput assays based on its colorimetric and fluorescent properties. Mixtures of different ratios of living and dead cells were prepared for a variety of bacteria. These mixtures were incubated with EB for 5 minutes, followed by the removal of unbound dye and the transfer of cells to a 96-well plate. $A_{530}$ measurements were collected and plotted for these different bacteria with each exhibiting a linear trend based on EB absorbance (FIG. 3). EB also functioned as a fluorescent bacterial cell viability indicator by clearly distinguishing between living and dead cells for diverse bacterial species using flow cytometry (FIG. 4). The extent of the fluorescence shift between live cells and dead cells did vary depending on the bacterial species (e.g., compare *E. coli* to *S. aureus*). These differences are likely due to either the relative cell size (larger cells will bind more dye) or inherent properties in the way in which EB binds to cellular materials. Together, these results demonstrate it is possible to rapidly estimate the amount of dead cells in a population based on EB absorbance (FIG. 3) and/or fluorescence (FIG. 4) in different high-throughput assays.

Figures 5A, 5B, 5C, 5D, 5E:
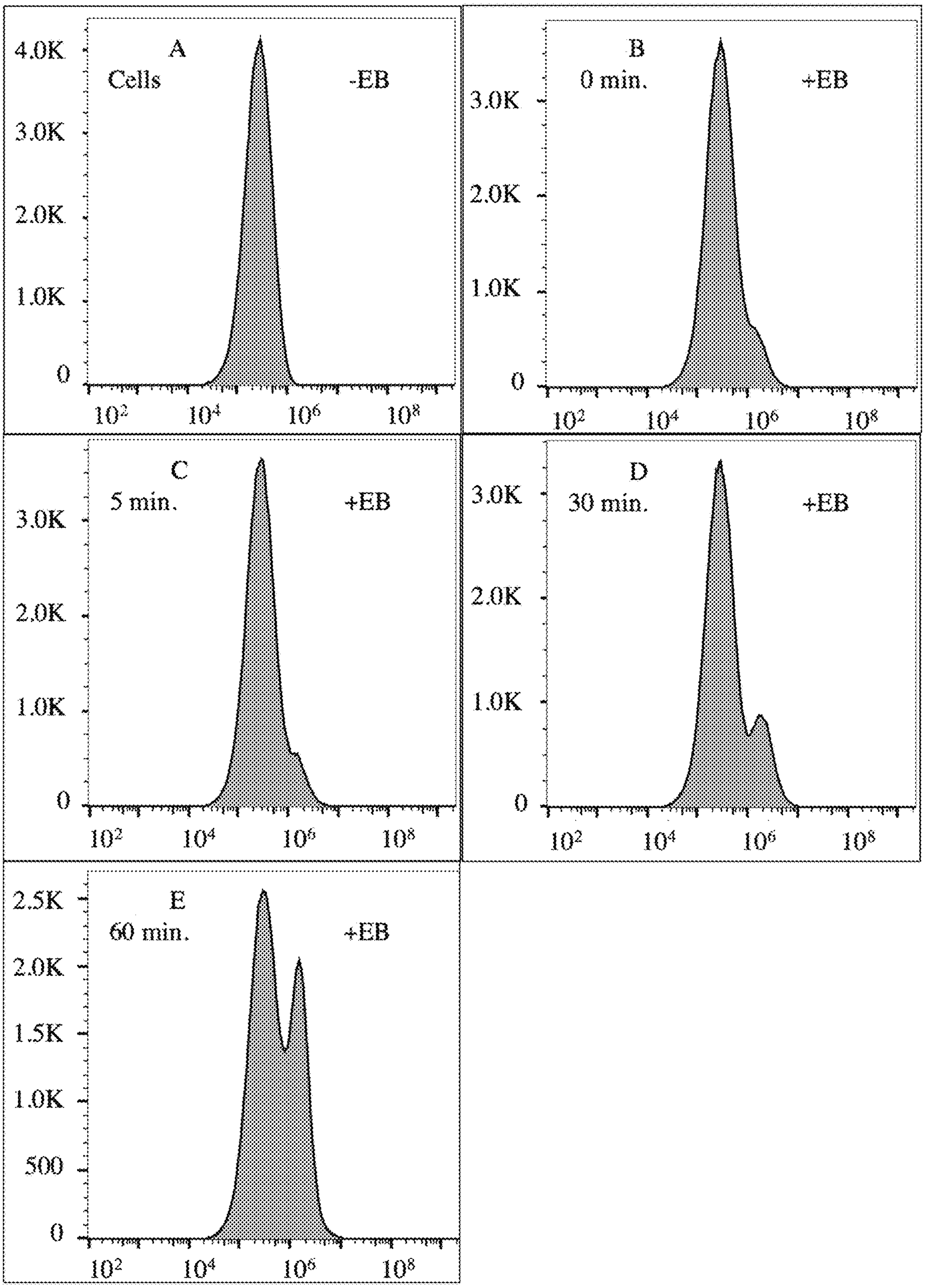
FIGS. 5A-5E: Monitoring cell viability in cultures exposed to a toxin. An *S. marcesans* culture was incubated with sodium azide and assayed for cell viability using EB at different time points. Prior to sodium azide addition two samples were taken from the culture and analyzed directly. One sample was not incubated with EB (top panel) while the other one was incubated with the dye (0 min. panel). At the indicated time points samples were taken from the culture, incubated with EB, and prepared for flow cytometry analysis. Over time, the relative amount of dye-positive cells in the culture increased. All flow cytometry plots indicate the number of cells analyzed on the Y-axis and the fluorescence intensity on the X-axis. 100,000 cells were analyzed for each plot.

To examine the ability of EB to assay changing cell viabilities in a bacterial culture, an *S. marcesans* culture was treated with a known toxin to Gram-negative bacteria-sodium azide (FIG. 5). Samples taken from the treated culture and examined by flow cytometry showed an increase in the amount of EB-positive cells over time. These results demonstrated that EB can detect changing cell viabilities rapidly and potentially be used to assay cell viability when screening possible anti-microbial agents.

All cell viability assays have limitations. The CFU method can overestimate the proportion of dead cells because any viable cells that are unable to divide, or dividing more slowly than wild-type, fail to form visible colonies and will be scored as dead. Membrane exclusion dyes, such as EB and propidium iodine, can underestimate the proportion of dead cells as recently dead cells may not have sufficiently compromised membranes to allow the dye to enter the cell. The sodium azide time course (FIG. 5) suggests that EB stains cells soon after dying. How other viability methods score dying cells also varies and it is often difficult to accurately quantitate, or distinguish, a dying cell population (4). For membrane-exclusion dyes, the concern is whether the dye enters cells with mildly compromised membranes that may be dying, but not dead. Chemical treatments that can mildly affect membrane permeability in bacteria (e.g., 20 mM EDTA, 0.1-0.5% TRITON™ X100, 0.12 M guanidine HCl or 0.1% SDS) did not result in an observable increase in dye-positive live cells. The results suggest that EB stains dead cells and not living cells with mildly compromised membranes.

Erythrosin B is the first, broadly applicable colorimetric vital dye for assaying viability in both Gram-positive and Gram-negative bacteria. The spectral properties of erythrosin B allow for its use in diverse experimental approaches with low-, medium-, and high-throughput assays. This versatile bacterial vital dye could significantly reduce the cost and time associated with doing viability studies on diverse bacterial species as well as experiments involving multiple species. Optimization of dye concentrations for different species is likely unnecessary as this is an individual dye that works well at a single concentration.

Unlike existing methods, the colorimetric properties of erythrosin B allow for rapid, straightforward live/dead determination by bright-field microscopy with a single dye. Importantly, its sensitivity allows for low rates of death to be accurately quantified. Erythrosin B has diverse commercial and academic applications such as studies screening for new anti-microbial compounds and determining the concentration of these needed for bactericidal effects. Erythrosin B staining may be particularly useful for field studies looking at diverse microbiomes, in field hospitals in the developing world where equipment and resources are limited, and in studying or identifying pathogenic bacteria which have entered a viable but nonculturable state (15). Lastly, while this study examined the utility of erythrosin B as an individual dye, future studies may identify important uses for it in bacterial viability studies as part of dye mixtures.

Example 2: Use of Adsorbent Resin to Remove Excess Erythrosin B (EB)

Figures 7A, 7B, 7C, 7D:
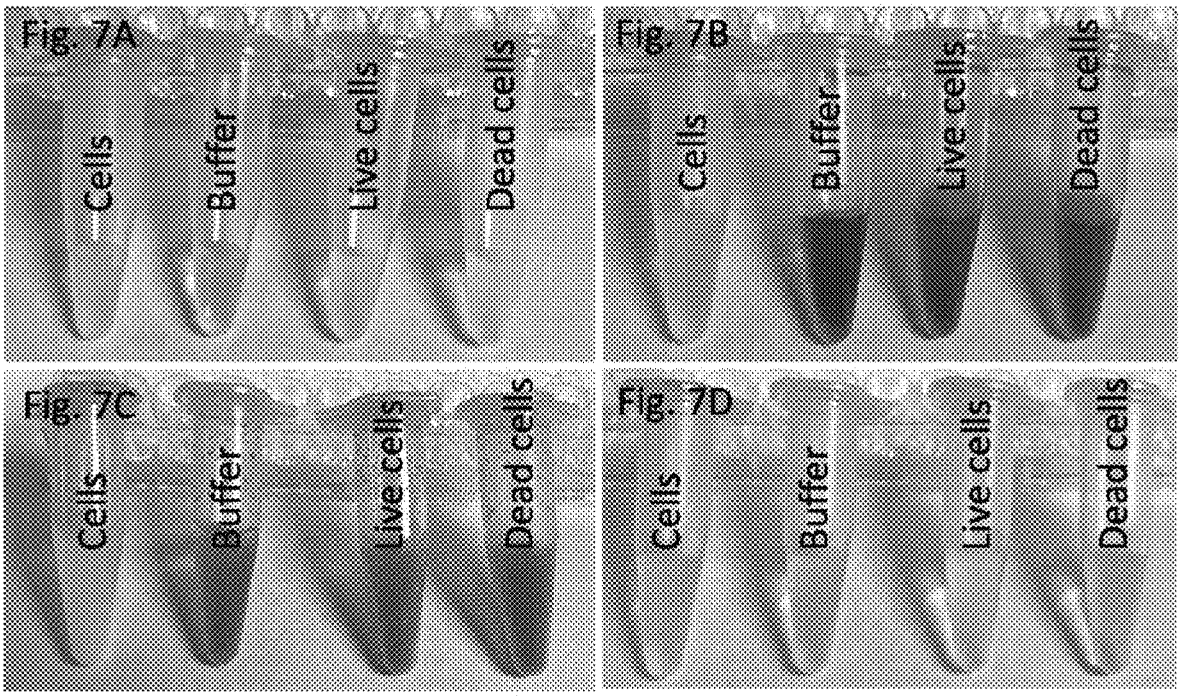
FIGS. 7A-7D: Inclusion of an adsorbent resin to cell solutions containing erythrosin B (EB) results in excess EB dye binding to the resin and dead bacterial cells retaining more EB dye than live bacterial cells.

The inclusion of an adsorbent to cell solutions containing erythrosin B (EB) results in excess EB dye binding to the adsorbent while bacterial cells retain the EB dye. Tubes containing solutions of bacterial cells (live or dead), as well as a buffer only tube, were incubated with EB dye and incubated at room temperature (FIG. 7). An adsorbent resin was added to all tubes followed by constant agitation via a vortexer at room temperature. After agitation, the tubes were left to allow resin to settle and then the solution containing non-adsorbed materials (cells and buffer) were transferred to new tubes (FIG. 7D). The solution containing the dead cells has a greater red color than the buffer (no cells) sample and the live cells sample.

Example 3: Plate Reading Assay to Determine Bacterial Cell Viability Using Erythrosin B (EB) and an Adsorbent A 5 mL overnight culture of desired bacteria (e.g., *E. coli* and *P. mirabilis*) were grown. The overnight culture was diluted 1:4 (250 microliters overnight in 750 microliters water or PBS) and the $OD_{600}$ was determined. A volume comparable to 0.75 OD was pipetted into four different 1.5 mL microfuge tubes. To 2 of these tubes an equal volume of 100% EtOH was added, and the tubes were inverted to mix. The tubes were subsequently incubated at 37° C. for 30 minutes. To the other 2 tubes an equal volume of PBS was added, and the tubes were inverted and then stored in the refrigerator.

After incubation, the tubes were centrifuged at 10,000 g for 3 minutes. The tubes were rotated and then centrifuged again. After centrifugation, the supernatant was removed from all tubes. One of the EtOH-treated tubes was resuspend with 0.5 mL of degassed PBS. After resuspension, this cell suspension was transferred to the second EtOH-treated tube and the pellet was resuspended. The other cell pellets were resuspended in a similar manner with degassed PBS. Each cell suspension was sonicated at 10% for 15 seconds. Control and different cell mixtures of live and dead (EtOH-treated) cells were prepared according to Table 1.

TABLE 1

% Live/% Dead cell mixtures for assaying

| % Live | Live Cells (microliters) | Dead Cells (microliters) | PBS (microliters) |
|---|---|---|---|
| Control | 0 | 0 | 100 |
| 100% | 100 | 0 | 0 |
| 75% | 75 | 25 | 0 |
| 50% | 50 | 50 | 0 |
| 25% | 25 | 75 | 0 |
| 0% | 0 | 100 | 0 |

Figure 8A:
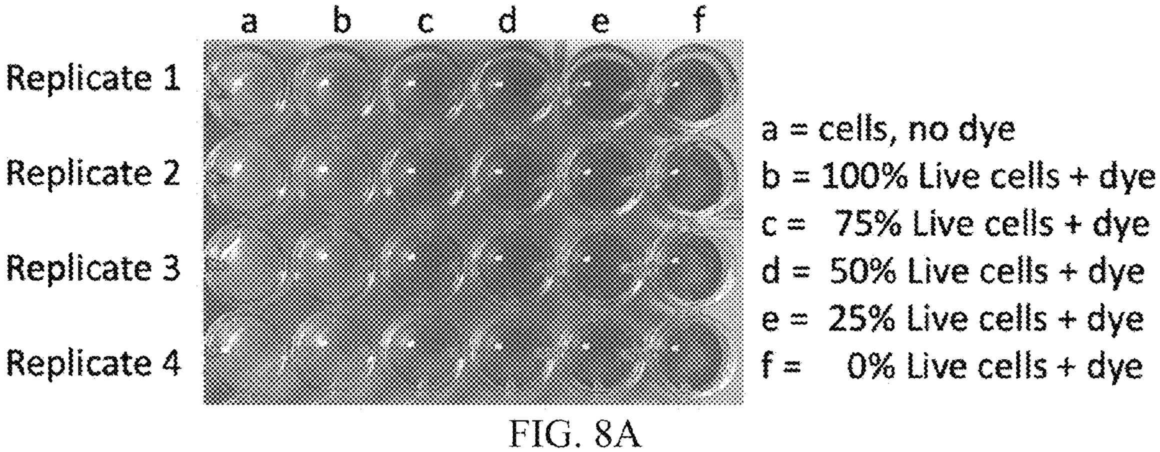
FIGS. 8A-8E: Use of an adsorbent after erythrosin B (EB) exposure recapitulates EB-only staining.
Figure 8B:
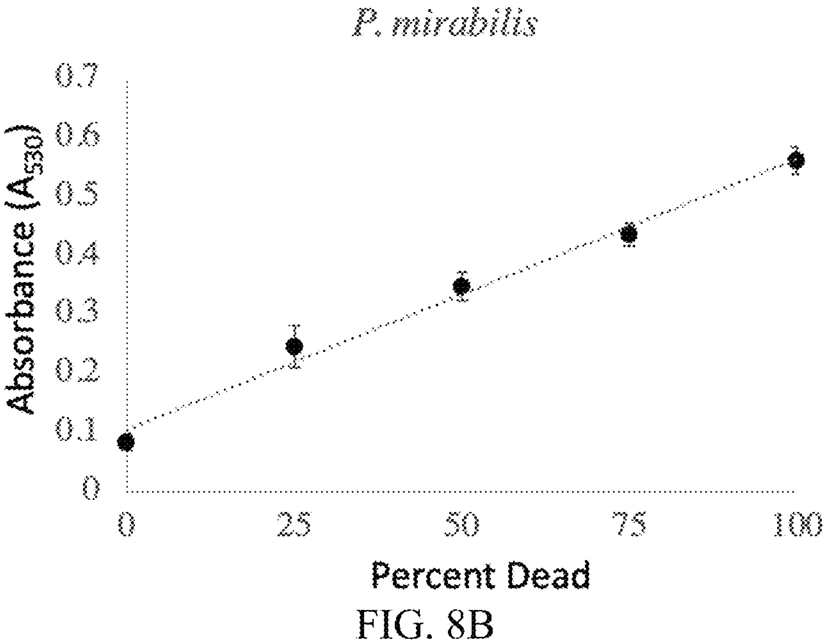
Figure 8C:
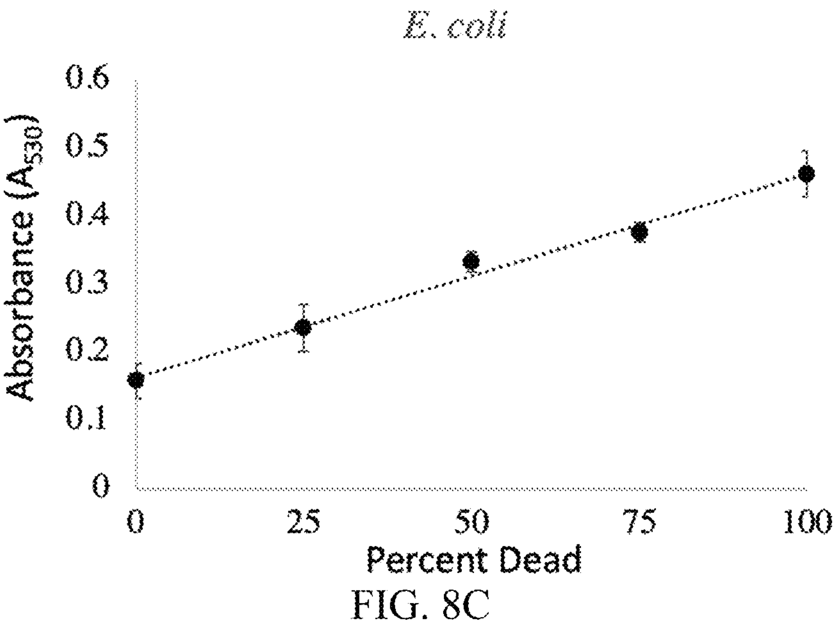
Figure 8D:
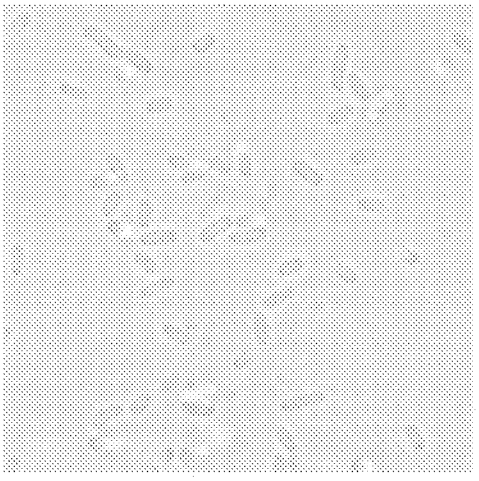
Figure 8E:
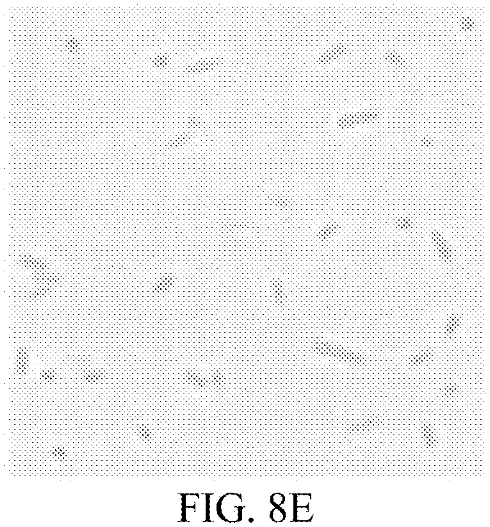
Figures 9A, 9B, 9C:
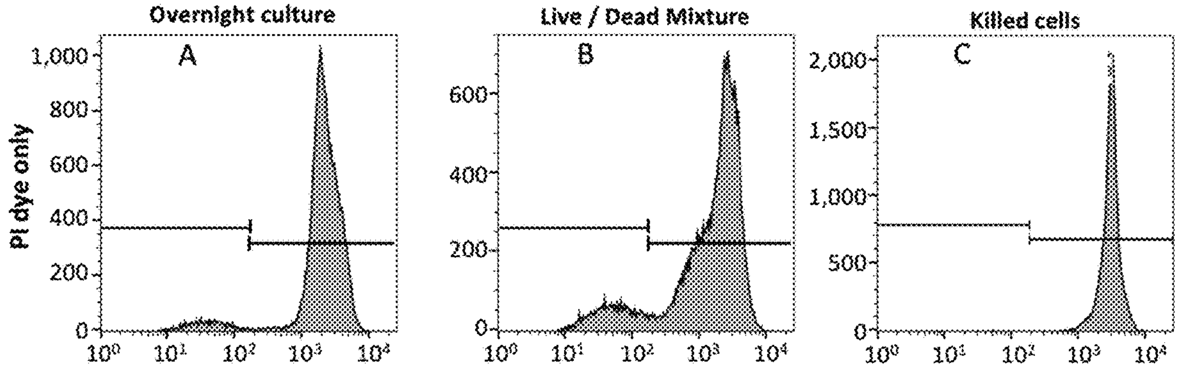
FIGS. 9A-F. Comparison of *Streptococcus mutans* viability as determined by propidium iodide (A-C) and an EB-based Kit (D-F). An overnight culture containing mostly live cells (>90% of these cells formed colonies in a colony forming unit assay), a near-equal mixture of live and dead cells, and a sample with ethanol-killed cells were stained with propidium iodide (PI; panels A-C respectively) and an EB-based kit (panels D-F respectively). All samples were analyzed by flow cytometry (30,000 events per sample). Horizontal bisector lines are drawn in each panel to indicate the dye-negative cells (left horizontal line) and the dye-positive cells (right horizontal line). In particular, note that virtually all cells in the overnight culture sample that were incubated with PI (Panel A) are considered dye-positive, or dead cells. When these overnight culture cells were analyzed using an EB-based kit (Panel D), >95% were dye-negative, or live cells, which was confirmed by a colony forming unit assay demonstrating that greater than 90% of these cells were alive. A similar overestimation of dead cells by propidium iodide is observed in the "Live/Dead Mixture" sample. Overall, the EB-based Kit provides a more accurate estimation of viability for *S. mutans.*
Figures 9D, 9E, 9F:
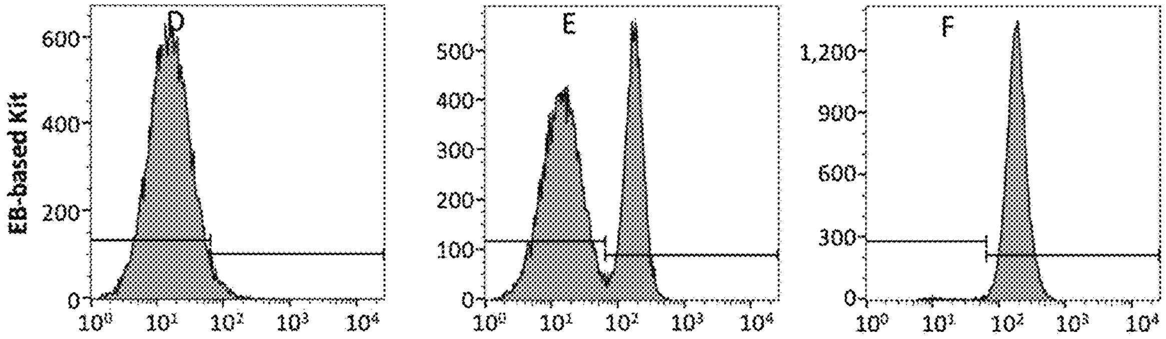
Figures 9G, 9H, 9I:
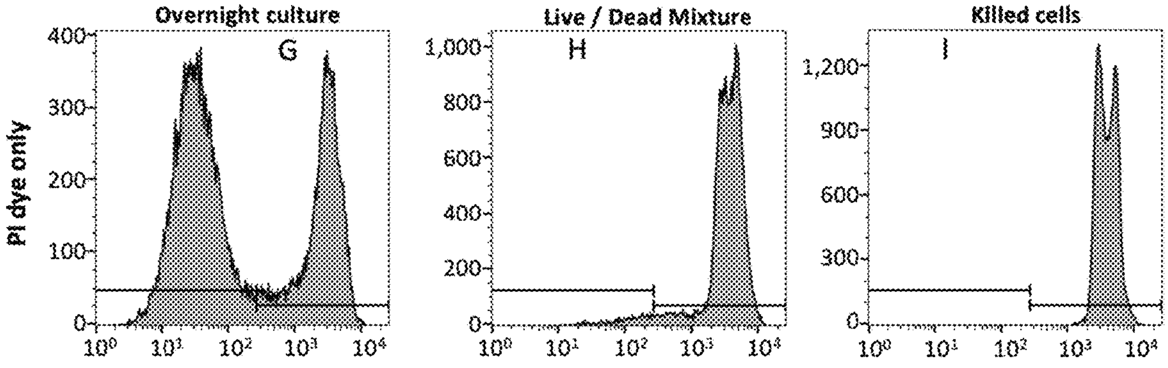
FIGS. 9G-L. Comparison of *Staphylococcus epidermidis* viability as determined by propidium iodide (G-I) and an EB-based Kit (J-L). An overnight culture containing mostly live cells (>90% of these cells formed colonies in a colony forming unit assay), a near-equal mixture of live and dead cells, and a sample with ethanol-killed cells were stained with propidium iodide (PI; panels G-I respectively) and an EB-based kit (panels G-J respectively). All samples were analyzed by flow cytometry (30,000 events per sample). Horizontal bisector lines are drawn in each panel to indicate the dye-negative cells (left horizontal line) and the dye-positive cells (right horizontal line). In particular, note that ~61% of cells in the overnight culture sample that were incubated with PI (Panel G) are considered dye-positive, or dead cells. When these overnight culture cells were analyzed using an EB-based kit (Panel J), >95% were dye-negative, or live cells, which was confirmed by a colony forming unit assay demonstrating that greater than 90% of these cells were alive. A similar overestimation of dead cells by propidium iodide is observed in the "Live/Dead Mixture" sample. In this mixture sample, the PI staining results show 95% of cells are dead, whereas the EB-based kit staining indicates 63% of cells are dead. Overall, the EB-based kit provides a more accurate estimation of viability for *S. epidermidis.*
Figures 9J, 9K, 9L:
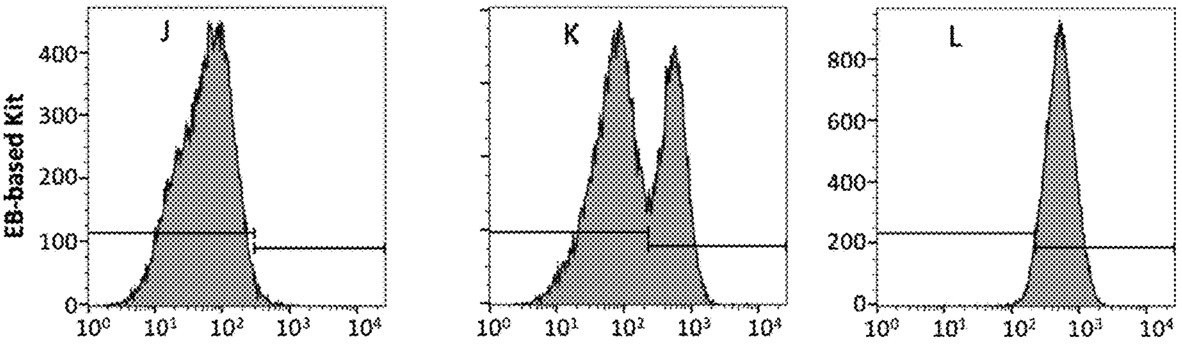
Figure 10A:
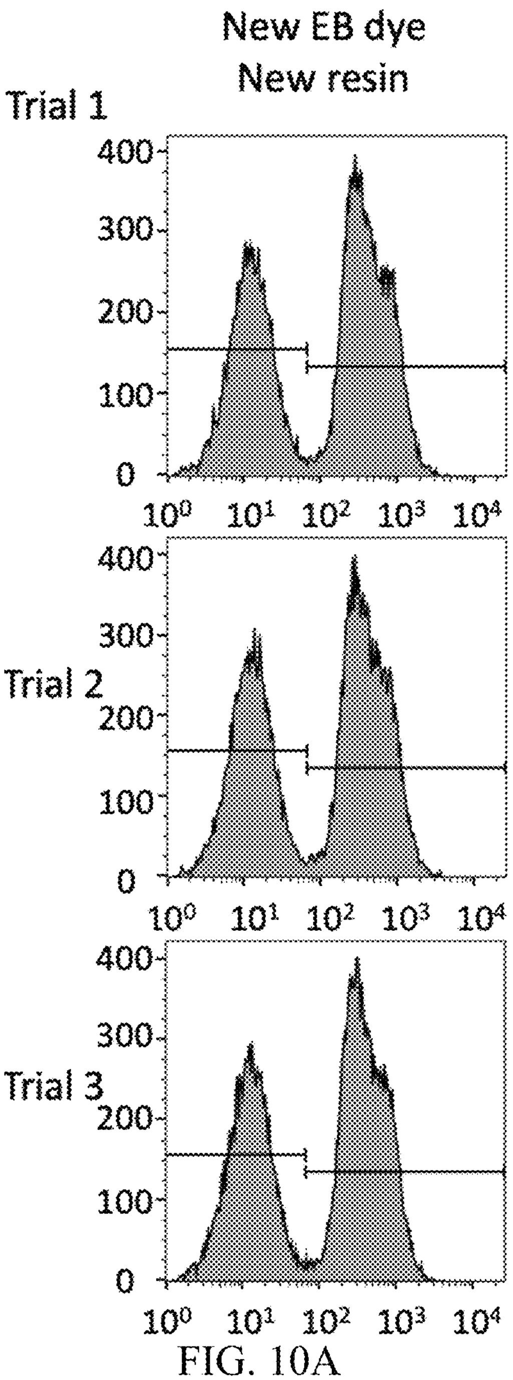
FIGS. 10A-D. Experiments to determine the shelf-life of different possible components of an EB dye-based bacterial viability kit. Triplicate experiments were performed on a mixture of live and dead *E. coli* cells with a newly prepared EB dye solution and a newly prepared adsorbent solution (FIG. 10A). Separate, triplicate experiments using the same *E. coli* mixture were performed to compare: a 12-month old EB dye solution with a newly prepared adsorbent solution (FIG. 10B), and a 6-month old adsorbent solution with a newly prepared EB dye solution (FIG. 10C). For each series of samples, the mean and standard deviation of the percent of cells that were dye-negative were determined (FIG. 10D).
Figure 10B:
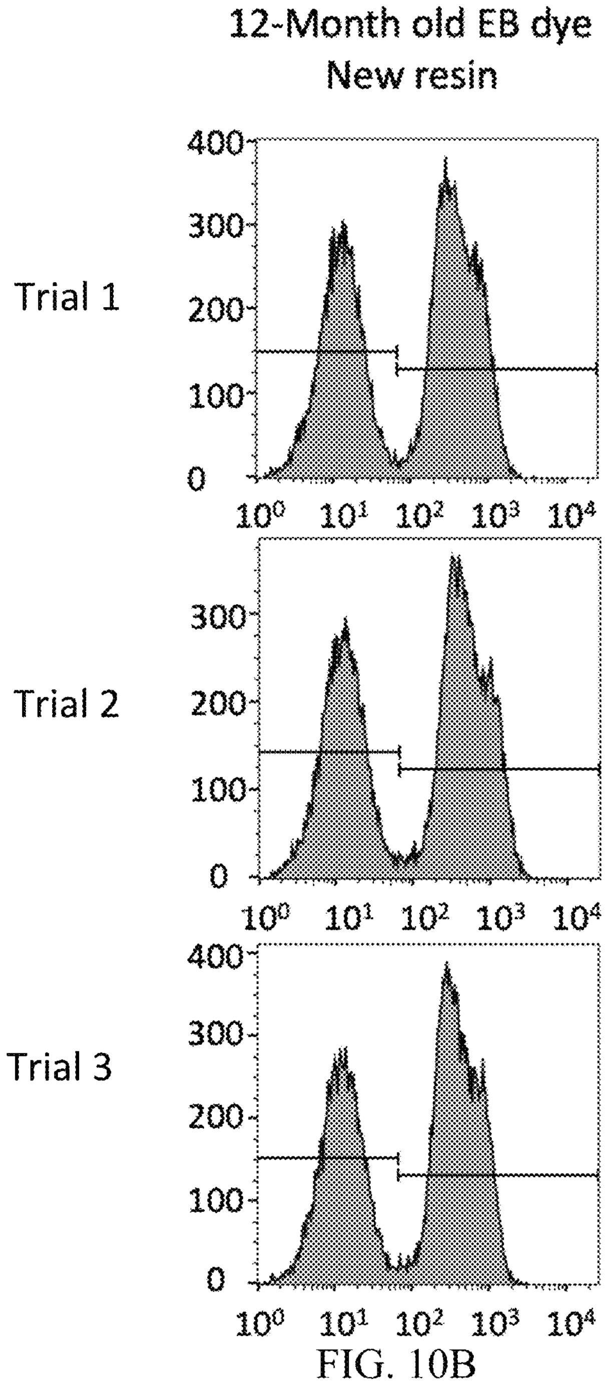
Figure 10C:
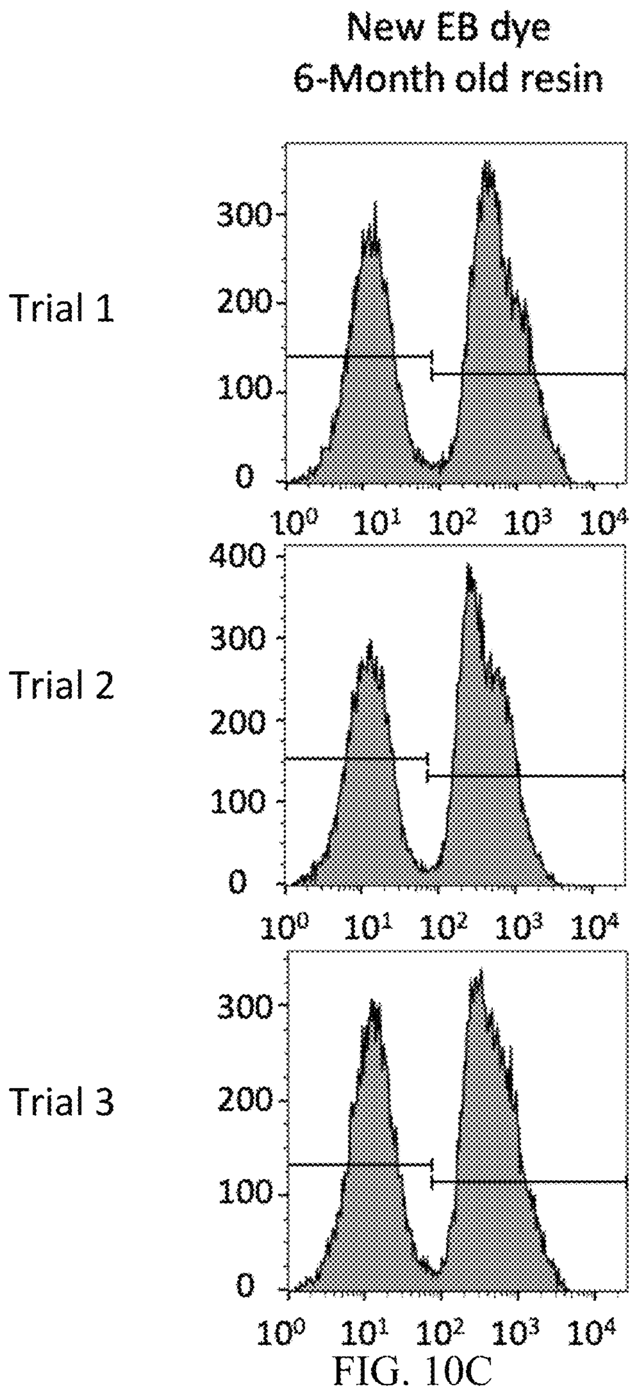
Figures 10D, 11:
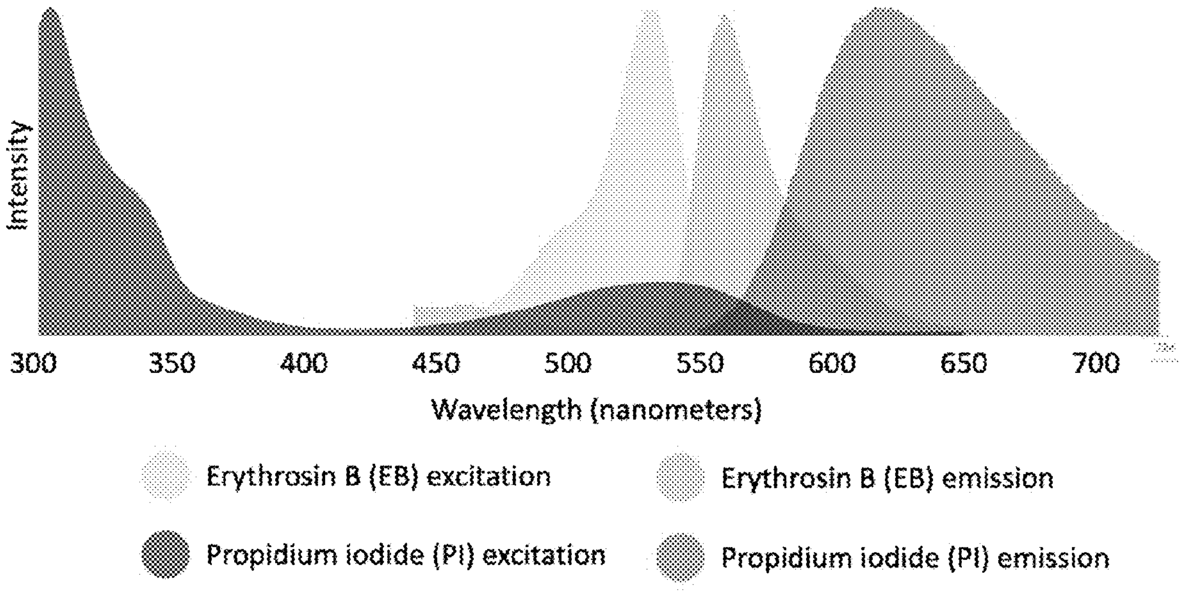
FIG. 11. The excitation and emission spectra for erythrosin B and propidium iodide, another cell viability dye that works by membrane exclusion, were compared. Erythrosin B has a narrow range for both excitation (approx. 480-550 nm) and emission (approx. 540-610 nm) compared to propidium iodide (excitation of approx. 300-350 nm and 475-575 nnm; emission of approx. 570-750 nm).

100 microliters of EB dye stock solution was added to each tube. The tube was briefly mixed/inverted and allowed to incubate for 5 minutes. 100 microliters of Chromalite PCG1200C (Purolite Corporation, King of Prussia, PA) was added to each tube, and the tube was mixed by vortexing for 5 minutes. The tubes were placed on the bench top and allowed to settle for 5 minutes. 200 microliters from each tube were transferred into a 96-well plate where a visible increase in the amount of EB dye can be observed by eye as the amount of dead cells increases (FIG. 8A). The 96-well plate was scanned at $A_{530}$, and the control value was subtracted from each data point. The results were then plotted as scatter plots (FIGS. 8B and 8C). EB cells from the 100% Live and 0% Live were viewed and imaged on a light microscope to compare the amount of visible dye associated with each sample (FIGS. 8D and 8E).

Example 4: Flow Cytometry Assay Shows that Erythrosin B (EB) and an Adsorbent can More Accurately Determine Bacterial Cell Viability in Bacteria which have Proved Challenging for Other Viability Dyes Determining bacterial cell viability by a different membrane exclusion dye (propidium iodide, PI) is not reliable for certain bacteria species and under certain growth conditions (10,11). Using an EB dye and adsorbent resin binding step (hereafter referred to as EB-based Kit), it is possible to reliably determine cell viability in these bacteria species (FIG. 9A-L). In these experiments, overnight cultures of *Streptococcus mutans* (FIG. 9A-F) and *Staphylococcus epidermidis* (FIG. 9G-L) were grown in Luria Broth. A portion of each culture was killed by treating with ethanol (50% ethanol, for 30 minutes at 30° C.). Overnight cells and ethanol-treated cells were centrifuged (10,000 g for 6 minutes) and then resuspended in phosphate buffered saline. Both cell suspensions were then sonicated to break apart any clusters (10% for 10 seconds). An approximately equal amount of the untreated, living overnight cells and the ethanol-treated, killed cells were mixed to generate a mixed population sample. 100 microliters of each sample (overnight culture, live/dead mixture, and killed cells) were incubated with 100 microliters of an EB-dye solution for 5 minutes. After incubation, 100 microliters of the adsorbent solution was added and gently agitated for 5 minutes on a vortexer. Following agitation, the tubes were left for 5 minutes to allow the adsorbent to settle and 200 microliters of the liquid solution above the adsorbent was transferred to a new tube. These samples were brought up to 1 mL in phosphate buffered saline. For propidium iodide staining, 40 microliters of the sonicated samples (overnight culture, live/dead mixture, and killed cells) were transferred to a fresh tube and brought up to 1 mL in phosphate buffered saline. 1 microliter of propidium iodide was added to each tube and incubated for 15 minutes before analyzing all samples by flow cytometry (FIGS. 9A-F for *Streptococcus mutans* and FIGS. 9G-L for *Staphylococcus epidermidis*).

These result show that that propidium iodide significantly overestimated the number of dead cells for both organisms in the overnight culture and the live/dead mixture sample. As a control, a colony forming unit assay was performed on the overnight culture sample and for both organisms it was found that >90% of these cells were alive.

Example 5: Comparing the Potential Shelf-Life of an EB Dye-Based and Adsorbent Kit to Propidium Iodide and their Spectral Properties To test how long both an EB dye solution and an adsorbent solution maintain function, tests were performed. For these experiments, a near-equal mixture of living *E. coli* cells from an overnight culture were mixed with ethanol-treated, killed *E. coli* cells. 100 microliters of this live/dead mixture was transferred into several different tubes. Separate experiments, done in triplicate, were done to compare dye that was 12-months old with fresh dye and a 6-month old adsorbent solution with a freshly made adsorbent solution (FIGS. 10A-D). For comparison, the manufacturer's stated shelf-life for another bacterial cell viability dye, propidium iodide (PI), is 6 to 12 months.

A comparison of the excitation and emission wavelengths of erythrosin B and propidium iodide shows that: i) a narrower band of wavelengths of light are needed to excite the EB dye compared to propidium iodide, and ii) that the EB dye emits fluorescence over a narrower range of wavelengths compared to propidium iodide. Many experiments involving fluorescent molecules, including viability assays, try to multiplex (use more than one fluorescent molecule at a time (e.g., FIG. 12)). A key limitation to the number of different fluorescent molecules that can be simultaneously used is the width of the region(s) of wavelengths for excitation and for emission. By having narrow ranges for both excitation and emission this allows erythrosin B to be more flexible than propidium iodide and potentially be paired with a wider variety of other fluorescent probes.

Figure 12A:
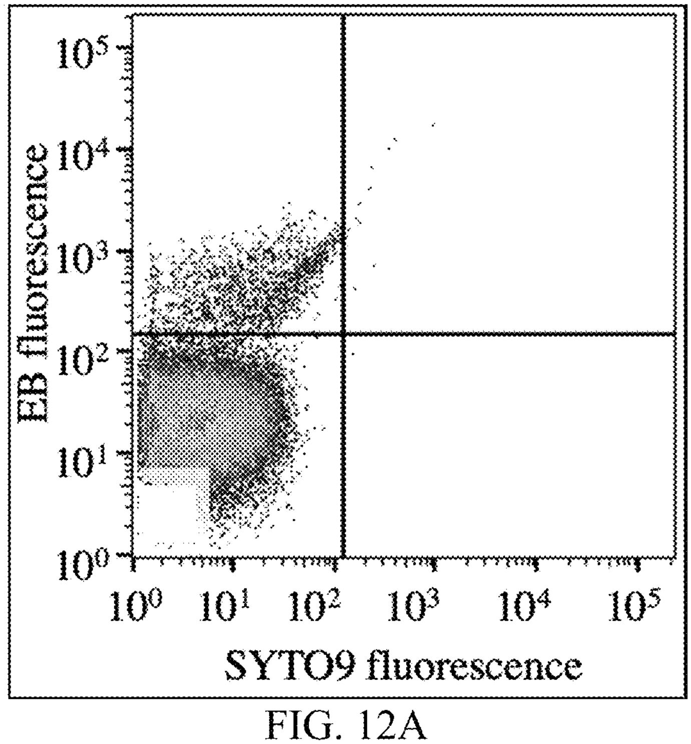
FIGS. 12A-12D. Erythrosin B (EB; Y-axis) can be used in combination with other fluorescent dyes (SYTO9™; X-axis). Live and dead *E. coli* cell populations were prepared.
Figure 12B:
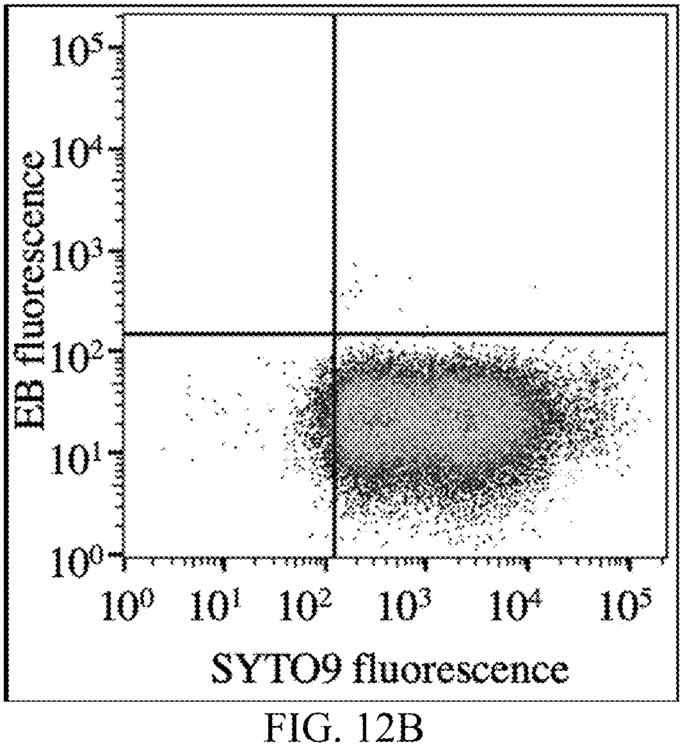
Figure 12C:
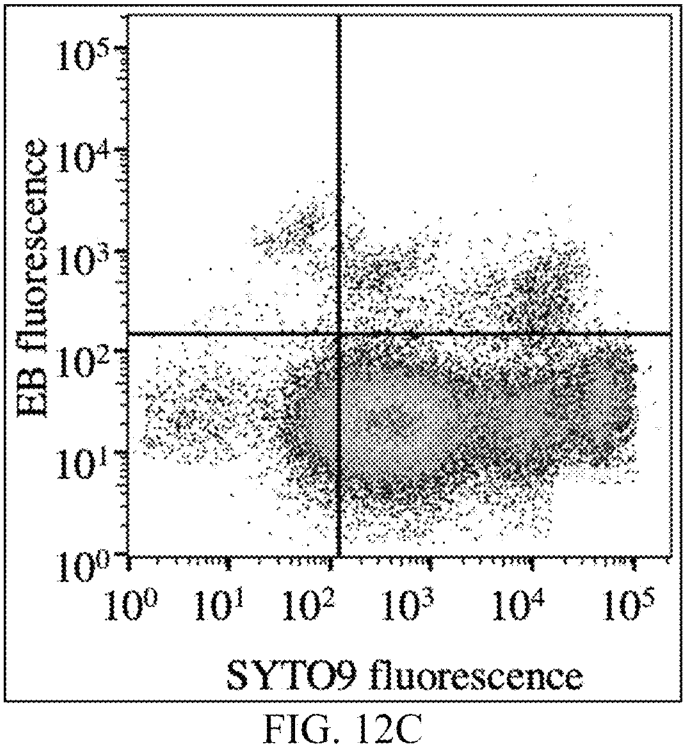
Figure 12D:
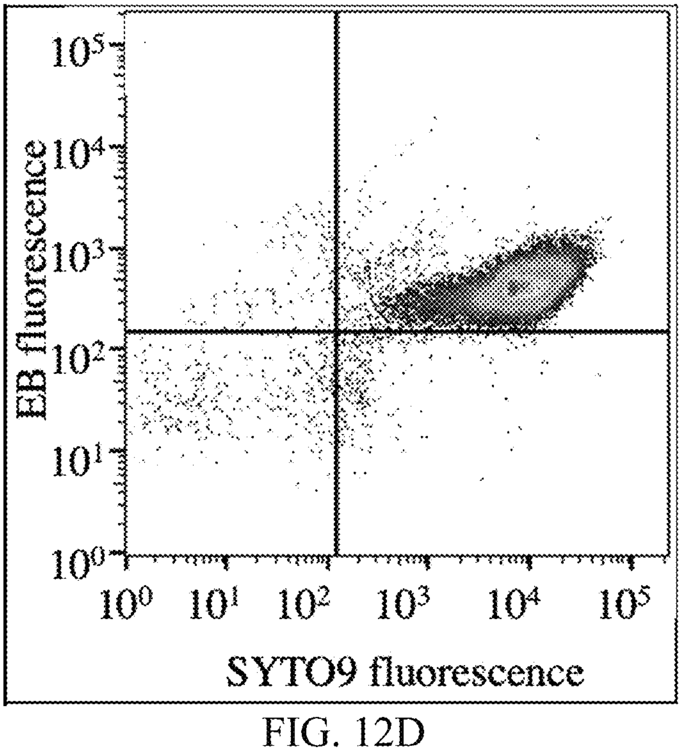
Figure 13:
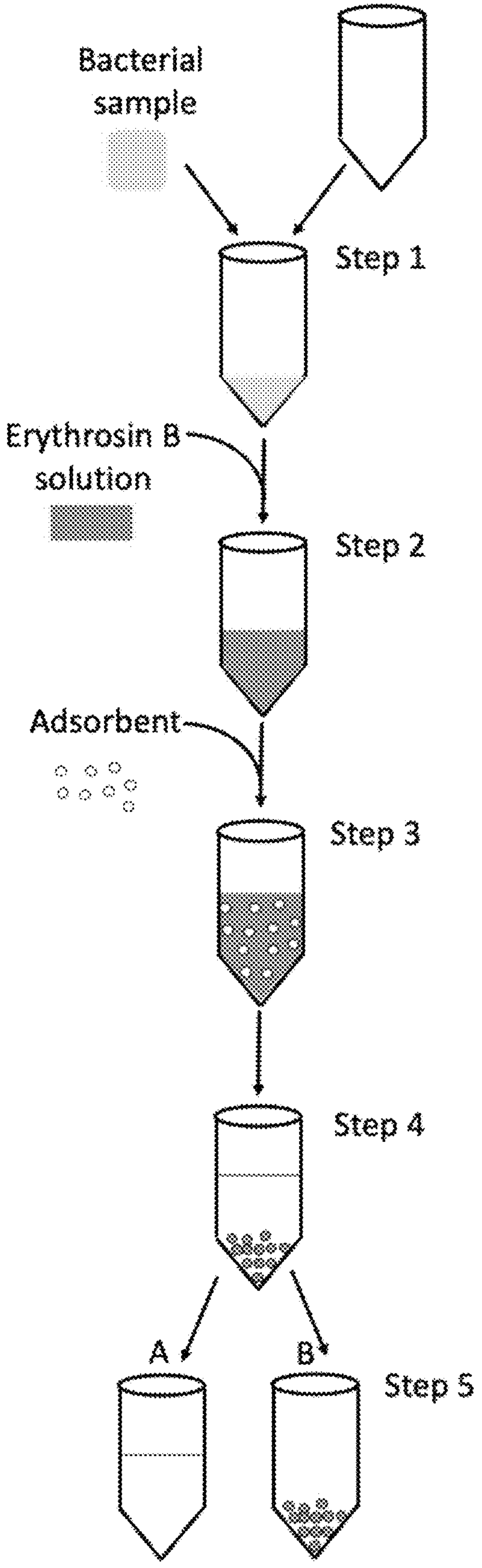
FIG. 13. Schematic of an erythrosin B based bacterial viability kit. In step 1, an amount of a bacterial sample is transferred into a tube/container (e.g., 100 microliters of a bacterial culture). In step 2, an amount of an erythrosin B solution is added to the tube/container and incubated for a period of time (e.g., 100 microliters of a 0.08% erythrosine B solution for 5 minutes at room temperature). In step 3, an amount of an adsorbent (powder, or in solution) is added to the tube/container and incubated for a period of time (e.g., 100 microliters of an adsorbent solution is gently agitated for 5 minutes at room temperature). In step 4, the solution is left for a period of time to allow the adsorbent, and not the bacteria, to settle to the bottom of the tube/container (e.g., wait 5 minutes at room temperature). In step 5, the erythrosin B stained bacterial solution is transferred to a fresh tube (A) which leaves the excess erythrosin B dye bound to the adsorbent in the original tube (B). The erythrosin B stained cells can then be analyzed for viability via colorimetric of fluorescent instruments (e.g., brightfield microscope, fluorescence microscope, plate reader, or flow cytometer). These cells can also be used in colony forming unit experiments as a comparator.

In some cell viability assays, it is advantageous to use more than one dye on a particular sample. To test if EB can be used in combination with other dyes, a common, DNA-staining bacterial dye (SYTO9™) was tested with EB. Live and dead *E. coli* cell samples were generated. After cells were incubated individually with dyes (EB or SYTO9™), or incubated simultaneously with both dyes, cells were analyzed by flow cytometry (FIG. 12). Both dyes functioned when incubated individually with cells (FIGS. 12A-C), and both dyes functioned when incubated together (FIG. 12D).

REFERENCES

1. Crowley L C, Marfell B J, Christensen M E, Waterhouse N J. Measuring Cell Death by Trypan Blue Uptake and Light Microscopy. *Cold Spring Harb Protoc,* 2016(7) (2016).
2. Crowley L C, Scott A P, Marfell B J, Boughaba J A, Chojnowski G, Waterhouse N J. Measuring Cell Death by Propidium Iodide Uptake and Flow Cytometry. *Cold Spring Harb Protoc,* 2016(7) (2016).
3. Altman S A, Randers L, Rao G. Comparison of trypan blue dye exclusion and fluorometric assays for mammalian cell viability determinations. *Biotechnol Prog,* 9(6), 671-674 (1993).
4. Kwolek-Mirek M, Zadrag-Tecza R. Comparison of methods used for assessing the viability and vitality of yeast cells. *FEMS Yeast Res,* 14(7), 1068-1079 (2014).
   This paper compares a variety of different methods used to determine viability in yeast and describes the benefits and drawbacks of each.
5. Boulos L, Prevost M, Barbeau B, Coallier J, Desjardins R. LIVE/DEAD BacLight: application of a new rapid staining method for direct enumeration of viable and total bacteria in drinking water. *J Microbiol Methods,* 37(1), 77-86 (1999).
6. Berney M, Hammes F, Bosshard F, Weilenmann H U, Egli T. Assessment and interpretation of bacterial viability by using the LIVE/DEAD BacLight Kit in combination with flow cytometry. *Applied and environmental microbiology,* 73(10), 3283-3290 (2007).
7. Virta M, Lineri S, Kankaanpaa P et al. Determination of complement-mediated killing of bacteria by viability staining and bioluminescence. *Applied and environmental microbiology,* 64(2), 515-519 (1998).
8. Stiefel P, Schmidt-Emrich S, Maniura-Weber K, Ren Q. Critical aspects of using bacterial cell viability assays with the fluorophores SYTO9™ and propidium iodide. *BMC Microbiol,* 15, 36 (2015).
9. Stocks S M. Mechanism and use of the commercially available viability stain, BacLight. *Cytometry A,* 61(2), 189-195 (2004).
10. Rosenberg M, Azevedo N F, Ivask A. Propidium iodide staining underestimates viability of adherent bacterial cells. *Sci Rep,* 9(1), 6483 (2019).
    This paper highlights one of the drawbacks of using propidium iodide staining (a key component of the BacLight™ kit) for determining bacterial cell viability.
11. Netuschil L, Auschill T M, Sculean A, Arweiler N B. Confusion over live/dead stainings for the detection of vital microorganisms in oral biofilms—which stain is suitable? *BMC Oral Health,* 14, 2 (2014).
12. Bhuyan B K, Loughman B E, Fraser T J, Day K J. Comparison of different methods of determining cell viability after exposure to cytotoxic compounds. *Exp Cell Res,* 97(2), 275-280 (1976).
13. Krause A W, Carley W W, Webb W W. Fluorescent erythrosin B is preferable to trypan blue as a vital exclusion dye for mammalian cells in monolayer culture. *J Histochem Cytochem,* 32(10), 1084-1090 (1984).
14. Wiegand S, Jogler M, Jogler C. On the maverick Planctomycetes. *FEMS Microbiol Rev,* 42(6), 739-760 (2018).
15. Oliver J D. Recent findings on the viable but nonculturable state in pathogenic bacteria. *FEMS Microbiol Rev,* 34(4), 415-425 (2010).
16. Kim A I, Kim H J, Lee H J, Lee K, Hong D, Lim H, Cho K, Jung N, and Yi Y W. *Analytical Biochemistry,* 492, 8-12 (2016).

The invention claimed is:

1. A kit for determining bacterial cell viability in a bacterial cell population, the kit comprising:

(a) erythrosin B (EB);

(b) an adsorbent capable of selectively binding EB and not bacterial cells; and (c) instructions for use, wherein the erythrosin B (EB) and adsorbent are used for determining bacterial cell viability in a bacterial cell population.

2. The kit of claim 1, wherein the kit further comprises a buffer.

3. The kit of claim 2, wherein the buffer is selected from a Tris buffer or a phosphate buffer.

4. The kit of claim 1, wherein the EB is in solution.

5. The kit of claim 4, wherein the concentration of EB solution is 0.01% to 0.5%.

6. The kit of claim 4, wherein the concentration of EB solution is 0.05% to 0.2%.

7. The kit of claim 4, wherein the concentration of EB solution is 0.08%.

8. The kit of claim 1, wherein the adsorbent comprises a hydrophobic moiety.

9. The kit of claim 8, wherein the hydrophobic moiety is selected from a divinylbenzene moiety or a polydivinylbenzene moiety.

10. The kit of claim 9, wherein the adsorbent is linked to a bead, a membrane, a plate, or a resin.

11. The kit of claim 10, wherein the adsorbent is linked to a bead.

12. A method of determining the percentage of dead bacteria in a bacterial cell population using the kit of claim 1, the method comprising:

(a) obtaining a bacterial cell population;

(b) contacting the bacterial cell population with an erythrosin B (EB) solution;

(c) contacting the bacterial cell population and EB with an adsorbent to remove excess EB;

(d) transferring the non-adsorbed bacterial cell population and EB solution; and (e) determining the percentage of dead bacteria in the bacterial cell population.

13. The method of claim 12, wherein the concentration of EB solution is 0.01% to 0.5%.

14. The method of claim 13, wherein the concentration of EB solution is 0.05% to 0.2%.

15. The method of claim 14, wherein the concentration of EB solution is 0.08%.

16. The method of claim 12, wherein the adsorbent comprises a hydrophobic moiety.

17. The method of claim 16, wherein the hydrophobic moiety is selected from a divinylbenzene moiety or a polydivinylbenzene moiety.

18. The method of claim 17, wherein the adsorbent is linked to a bead, a membrane, a plate, or a resin.

19. The method of claim 18, wherein the adsorbent is linked to a bead.

20. The method of claim 16, wherein the adsorbent is 0.08 mg/mL to 2.0 mg/mL.

21. The method of claim 12, wherein the method further comprises a step of contacting the transferred non-adsorbed bacterial cell population and EB solution with an event marker.

22. The method of claim 21, wherein the event marker is selected from a DNA binding marker, a metabolic marker, a cell surface marker, or a general fluorescent marker.

23. The method of claim 12, wherein a plate reader, a flow cytometer, an automated cell counter, or a microscope is used to determine the percentage of bacteria in the bacterial cell population.

* * * * *